US012742012B2

(12) United States Patent
Ren et al.

(10) Patent No.: US 12,742,012 B2
(45) **Date of Patent: *Sep. 22, 2026**

(54) HUMANIZED ANTI-TRKA ANTIBODIES AND USES THEREOF

(71) Applicant: SUNSHINE LAKE PHARMA CO., LTD., Dongguan (CN)

(72) Inventors: Zhiheng Ren, Dongguang (CN); Junji Dong, Dongguang (CN); Zhuandi He, Dongguang (CN); Kezhu Wang, Dongguang (CN); Jielian Lu, Dongguang (CN); Shushan Lin, Dongguang (CN); Liang Liu, Dongguang (CN); Xiang Li, Dongguang (CN); Kuo Zhang, Dongguang (CN); Yan Jiang, Dongguang (CN); Xiaoping Li, Dongguang (CN); Xiaofeng Chen, Dongguang (CN); Wenjia Li, Dongguang (CN)

(73) Assignee: SUNSHINE LAKE PHARMA CO., LTD., Dongguan (CN)

( * ) Notice: Subject to any disclaimer, the term of this patent is extended or adjusted under 35 U.S.C. 154(b) by 935 days.

This patent is subject to a terminal disclaimer.

(21) Appl. No.: 17/911,571

(22) PCT Filed: Nov. 18, 2021

(86) PCT No.: PCT/CN2021/131343

§ 371 (c)(1),
(2) Date: Sep. 14, 2022

(87) PCT Pub. No.: WO2022/105814

PCT Pub. Date: May 27, 2022

(65) Prior Publication Data

US 2023/0357411 A1 Nov. 9, 2023

(30) Foreign Application Priority Data

Nov. 20, 2020 (CN) ........................ 202011307482.7

(51) Int. Cl.

| | |
|---|---|
| ***C07K 16/28*** | (2006.01) |
| ***A61P 43/00*** | (2006.01) |
| ***C12N 15/63*** | (2006.01) |
| ***G01N 33/74*** | (2006.01) |

(52) U.S. Cl.
CPC .......... *C07K 16/2863* (2013.01); *A61P 43/00* (2018.01); *C12N 15/63* (2013.01); *G01N 33/74* (2013.01); *C07K 2317/24* (2013.01); *C07K 2317/52* (2013.01); *C07K 2317/565* (2013.01)

(58) Field of Classification Search
None
See application file for complete search history.

(56) References Cited

U.S. PATENT DOCUMENTS

| | | | |
|---|---|---|---|
| 9,751,947 | B2 | 9/2017 | Benigni et al. |
| 2013/0344064 | A1 | 12/2013 | Blein et al. |
| 2015/0183885 | A1 | 7/2015 | Blein et al. |
| 2016/0319027 | A1 | 11/2016 | Blein et al. |
| 2017/0218087 | A1 | 8/2017 | Blein et al. |
| 2017/0362327 | A1 | 12/2017 | Walmsley et al. |

OTHER PUBLICATIONS

O-Sullivan et al., Int. J. Mol. Sci. 2022, 23, 12076—23 pages total (Year: 2022).*
Antoine Gardin and Giuseppe Ronzitti, Archives de Pédiatrie 30 (2023) 8S46-8S52 (Year: 2023).*
Feb. 15, 2022 International Search Report issued in Patent Application No. PCT/CN2021/131343.
Feb. 15, 2022 Written Opinion of the International Searchiong Authority issued in Patent Application No. PCT/CN2021/131343.

* cited by examiner

*Primary Examiner* — Christina M Borgeest
(74) *Attorney, Agent, or Firm* — Oliff PLC

(57) ABSTRACT

A humanized antibody or antigen-binding fragment thereof capable of specifically recognizing TrkA and uses thereof. The antibody includes a heavy chain variable region with an amino acid sequence shown in any one of SEQ ID NO: 2-8, and a light chain variable region with an amino acid sequence shown in any one of SEQ ID NO: 10-13. The above-mentioned antibody according to the embodiments of the present invention can specifically target and bind to the TrkA receptor and block the binding of NGF and TrkA.

17 Claims, 6 Drawing Sheets

Specification includes a Sequence Listing.

| McAb | H0L0-IgG4 | H1L1-IgG4 | H3L1-IgG4 | H3L2-IgG4 |
|---|---|---|---|---|
| EC50 | 0.08669 | 0.1307 | 0.1268 | 0.1683 |

| McAb | H0L0-IgG4 | H1L1-IgG4 | H3L1-IgG4 | H3L2-IgG4 |
|---|---|---|---|---|
| EC50 | 0.1048 | 0.1341 | 0.1110 | 0.1254 |

| McAb | H0L0-IgG4 | H1L1-IgG4 | H3L1-IgG4 | H3L2-IgG4 |
|---|---|---|---|---|
| IC50 | 0.8810 | 0.7963 | 0.7405 | 0.6653 |

| McAb | H0L0-IgG4 | H1L1-IgG4 | H3L1-IgG4 | H3L2-IgG4 |
|---|---|---|---|---|
| IC50 | 0.3959 | 0.3848 | 0.2826 | 0.2524 |

SEQUENCE LISTING

<160> NUMBER OF SEQ ID NOS: 49

<210> SEQ ID NO 1
<211> LENGTH: 116
<212> TYPE: PRT
<213> ORGANISM: Artificial Sequence
<220> FEATURE:
<223> OTHER INFORMATION: Heavy chain variable region

<400> SEQUENCE: 1

```
Gln Val Gln Leu Gln Gln Ser Gly Ala Glu Leu Val Arg Pro Gly Thr
1               5                   10                  15

Ser Val Lys Ile Ser Cys Lys Ala Ser Gly Tyr Ala Phe Thr Asn Tyr
            20                  25                  30

Trp Leu Gly Trp Met Lys Gln Arg Pro Gly His Gly Leu Glu Trp Ile
        35                  40                  45

Gly Asp Phe Tyr Pro Arg Thr Gly Asn Thr Phe Tyr Asn Glu Asn Phe
    50                  55                  60

Lys Gly Lys Val Thr Leu Thr Ala Asp Lys Ser Ser Asn Thr Ala Tyr
65                  70                  75                  80

Met Gln Leu Ser Ser Leu Thr Ser Glu Asp Ser Ala Val Tyr Leu Cys
                85                  90                  95

Ala Arg Ala Gly Thr Gly Phe Asp Tyr Trp Gly Gln Gly Thr Thr Leu
            100                 105                 110

Thr Val Ser Ser
        115
```

<210> SEQ ID NO 2
<211> LENGTH: 116
<212> TYPE: PRT
<213> ORGANISM: Artificial Sequence
<220> FEATURE:
<223> OTHER INFORMATION: Heavy chain variable region

<400> SEQUENCE: 2

```
Glu Val Gln Leu Leu Glu Ser Gly Gly Gly Leu Val Gln Pro Gly Gly
1               5                   10                  15

Ser Leu Lys Leu Ser Cys Lys Ala Ser Gly Tyr Ala Phe Thr Asn Tyr
            20                  25                  30

Trp Leu Gly Trp Met Lys Gln Arg Pro Gly His Gly Leu Glu Trp Ile
        35                  40                  45

Gly Asp Phe Tyr Pro Arg Thr Gly Asn Thr Phe Tyr Asn Glu Asn Phe
    50                  55                  60

Lys Gly Lys Val Thr Leu Thr Ala Asp Lys Ser Ser Asn Thr Ala Tyr
65                  70                  75                  80

Met Gln Leu Ser Ser Leu Thr Ser Glu Asp Ser Ala Val Tyr Leu Cys
                85                  90                  95

Ala Arg Ala Gly Thr Gly Phe Asp Tyr Trp Gly Gln Gly Thr Thr Leu
            100                 105                 110

Thr Val Ser Ser
        115
```

<210> SEQ ID NO 3
<211> LENGTH: 116
<212> TYPE: PRT
<213> ORGANISM: Artificial Sequence
<220> FEATURE:
<223> OTHER INFORMATION: Heavy chain variable region

<400> SEQUENCE: 3

```
Glu Val Gln Leu Leu Glu Ser Gly Gly Gly Leu Val Gln Pro Gly Gly
1               5                   10                  15

Ser Leu Lys Leu Ser Cys Lys Ala Ser Gly Tyr Ala Phe Thr Asn Tyr
            20                  25                  30

Trp Leu Gly Trp Met Lys Gln Arg Pro Gly His Gly Leu Glu Trp Ile
        35                  40                  45

Gly Gly Phe Tyr Pro Arg Thr Gly Asn Thr Phe Tyr Asn Glu Asn Phe
    50                  55                  60

Lys Gly Lys Val Thr Leu Thr Ala Asp Lys Ser Ser Asn Thr Ala Tyr
65                  70                  75                  80

Met Gln Leu Ser Ser Leu Thr Ser Glu Asp Ser Ala Val Tyr Leu Cys
                85                  90                  95

Ala Arg Ala Gly Thr Gly Phe Asp Tyr Trp Gly Gln Gly Thr Thr Leu
            100                 105                 110

Thr Val Ser Ser
        115


<210> SEQ ID NO 4
<211> LENGTH: 116
<212> TYPE: PRT
<213> ORGANISM: Artificial Sequence
<220> FEATURE:
<223> OTHER INFORMATION: Heavy chain variable region

<400> SEQUENCE: 4

Glu Val Gln Leu Leu Glu Ser Gly Gly Gly Leu Val Gln Pro Gly Gly
1               5                   10                  15

Ser Leu Lys Leu Ser Cys Lys Ala Ser Gly Tyr Ala Phe Thr Asn Tyr
            20                  25                  30

Trp Leu Gly Trp Met Lys Gln Arg Pro Gly His Gly Leu Glu Trp Ile
        35                  40                  45

Gly Asp Phe Tyr Pro Arg Thr Gly Asn Thr Phe Tyr Asn Glu Asn Phe
    50                  55                  60

Lys Gly Gln Val Thr Met Ser Val Asp Lys Ser Ile Thr Thr Ala Tyr
65                  70                  75                  80

Leu Gln Trp Asn Ser Leu Lys Ala Ser Asp Thr Ala Met Tyr Tyr Cys
                85                  90                  95

Ala Arg Ala Gly Thr Gly Phe Asp Tyr Trp Gly Gln Gly Thr Thr Leu
            100                 105                 110

Thr Val Ser Ser
        115


<210> SEQ ID NO 5
<211> LENGTH: 116
<212> TYPE: PRT
<213> ORGANISM: Artificial Sequence
<220> FEATURE:
<223> OTHER INFORMATION: Heavy chain variable region

<400> SEQUENCE: 5

Gln Val Gln Leu Val Gln Ser Gly Val Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Trp Leu Gly Trp Met Lys Gln Arg Pro Gly His Gly Leu Glu Trp Ile
        35                  40                  45

Gly Asp Phe Tyr Pro Arg Thr Gly Asn Thr Phe Tyr Asn Glu Asn Phe
```

```
    50                  55                  60

Lys Gly Gln Val Thr Met Ser Val Asp Lys Ser Ile Thr Thr Ala Tyr
65                  70                  75                  80

Leu Gln Trp Asn Ser Leu Lys Ala Ser Asp Thr Ala Met Tyr Tyr Cys
                85                  90                  95

Ala Arg Ala Gly Thr Gly Phe Asp Tyr Trp Gly Gln Gly Thr Thr Leu
            100                 105                 110

Thr Val Ser Ser
        115


<210> SEQ ID NO 6
<211> LENGTH: 116
<212> TYPE: PRT
<213> ORGANISM: Artificial Sequence
<220> FEATURE:
<223> OTHER INFORMATION: Heavy chain variable region

<400> SEQUENCE: 6

Gln Val Gln Leu Val Gln Ser Gly Val Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Trp Leu Gly Trp Met Lys Gln Arg Pro Gly His Gly Leu Glu Trp Ile
        35                  40                  45

Gly Asp Phe Tyr Pro Arg Thr Gly Asn Thr Phe Tyr Asn Glu Asn Phe
    50                  55                  60

Lys Gly Lys Val Thr Ile Thr Ala Asp Lys Ser Ile Thr Thr Ala Tyr
65                  70                  75                  80

Met Gln Leu Ser Ser Leu Lys Ala Ser Asp Thr Ala Val Tyr Tyr Cys
                85                  90                  95

Ala Arg Ala Gly Thr Gly Phe Asp Tyr Trp Gly Gln Gly Thr Thr Leu
            100                 105                 110

Thr Val Ser Ser
        115


<210> SEQ ID NO 7
<211> LENGTH: 116
<212> TYPE: PRT
<213> ORGANISM: Artificial Sequence
<220> FEATURE:
<223> OTHER INFORMATION: Heavy chain variable region

<400> SEQUENCE: 7

Gln Val Gln Leu Val Gln Ser Gly Val Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Trp Leu Gly Trp Val Lys Gln Arg Pro Gly His Gly Leu Glu Trp Ile
        35                  40                  45

Gly Asp Phe Tyr Pro Arg Thr Gly Asn Thr Phe Tyr Asn Glu Asn Phe
    50                  55                  60

Lys Gly Lys Val Thr Ile Thr Ala Asp Lys Ser Ile Thr Thr Ala Tyr
65                  70                  75                  80

Met Gln Leu Ser Ser Leu Lys Ala Ser Asp Thr Ala Val Tyr Tyr Cys
                85                  90                  95

Ala Arg Ala Gly Thr Gly Phe Asp Tyr Trp Gly Gln Gly Thr Thr Leu
            100                 105                 110
```

```
Thr Val Ser Ser
        115


<210> SEQ ID NO 8
<211> LENGTH: 116
<212> TYPE: PRT
<213> ORGANISM: Artificial Sequence
<220> FEATURE:
<223> OTHER INFORMATION: Heavy chain variable region

<400> SEQUENCE: 8

Gln Val Gln Leu Val Gln Ser Gly Val Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Trp Leu Gly Trp Met Lys Gln Arg Pro Gly His Gly Leu Glu Trp Ile
        35                  40                  45

Gly Asp Phe Tyr Pro Arg Thr Gly Asn Thr Phe Tyr Asn Glu Asn Phe
    50                  55                  60

Lys Gly Lys Val Thr Leu Thr Ala Asp Lys Ser Ser Asn Thr Ala Tyr
65                  70                  75                  80

Met Gln Leu Ser Ser Leu Thr Ser Glu Asp Ser Ala Val Tyr Leu Cys
                85                  90                  95

Ala Arg Ala Gly Thr Gly Phe Asp Tyr Trp Gly Gln Gly Thr Thr Leu
            100                 105                 110

Thr Val Ser Ser
        115


<210> SEQ ID NO 9
<211> LENGTH: 107
<212> TYPE: PRT
<213> ORGANISM: Artificial Sequence
<220> FEATURE:
<223> OTHER INFORMATION: Light chain variable region

<400> SEQUENCE: 9

Ser Ile Val Met Thr Gln Ser Pro Lys Ser Met Ser Met Ser Val Gly
1               5                   10                  15

Glu Arg Val Thr Leu Ser Cys Lys Ala Ser Glu Asn Val Gly Gly Tyr
            20                  25                  30

Val Ser Trp Tyr Gln Gln Lys Pro Asp Gln Ser Pro Lys Leu Leu Ile
        35                  40                  45

Tyr Gly Ala Ser Ser Arg His Thr Gly Val Pro Asp Arg Phe Thr Gly
    50                  55                  60

Ser Gly Ser Glu Thr Asp Phe Thr Leu Thr Ile Ser Ser Val Gln Ala
65                  70                  75                  80

Glu Asp Leu Ala Ala Tyr His Cys Gly Gln Asn Tyr Ile Tyr Pro Phe
                85                  90                  95

Thr Phe Gly Gly Gly Thr Lys Leu Glu Ile Lys
            100                 105


<210> SEQ ID NO 10
<211> LENGTH: 107
<212> TYPE: PRT
<213> ORGANISM: Artificial Sequence
<220> FEATURE:
<223> OTHER INFORMATION: Light chain variable region

<400> SEQUENCE: 10

Glu Ile Val Met Thr Gln Ser Pro Ala Thr Leu Ser Leu Ser Val Gly
```

```
1               5                   10                  15

Glu Arg Val Thr Leu Ser Cys Lys Ala Ser Glu Asn Val Gly Gly Tyr
            20                  25                  30

Val Ser Trp Tyr Gln Gln Lys Pro Asp Gln Ser Pro Lys Leu Leu Ile
        35                  40                  45

Tyr Gly Ala Ser Ser Arg His Thr Gly Val Pro Asp Arg Phe Thr Gly
    50                  55                  60

Ser Gly Ser Glu Thr Asp Phe Thr Leu Thr Ile Ser Ser Val Gln Ala
65                  70                  75                  80

Glu Asp Leu Ala Ala Tyr His Cys Gly Gln Asn Tyr Ile Tyr Pro Phe
                85                  90                  95

Thr Phe Gly Gly Gly Thr Lys Leu Glu Ile Lys
            100                 105


<210> SEQ ID NO 11
<211> LENGTH: 107
<212> TYPE: PRT
<213> ORGANISM: Artificial Sequence
<220> FEATURE:
<223> OTHER INFORMATION: Light chain variable region

<400> SEQUENCE: 11

Glu Ile Val Met Thr Gln Ser Pro Ala Thr Leu Ser Leu Ser Val Gly
1               5                   10                  15

Glu Arg Val Thr Leu Ser Cys Lys Ala Ser Glu Asn Val Gly Gly Tyr
            20                  25                  30

Val Ser Trp Tyr Gln Gln Lys Pro Asp Gln Ser Pro Lys Leu Leu Ile
        35                  40                  45

Tyr Gly Ala Ser Ser Arg Ala Thr Gly Val Pro Asp Arg Phe Thr Gly
    50                  55                  60

Ser Gly Ser Glu Thr Asp Phe Thr Leu Thr Ile Ser Ser Val Gln Ala
65                  70                  75                  80

Glu Asp Leu Ala Ala Tyr His Cys Gly Gln Asn Tyr Ile Tyr Pro Phe
                85                  90                  95

Thr Phe Gly Gly Gly Thr Lys Leu Glu Ile Lys
            100                 105


<210> SEQ ID NO 12
<211> LENGTH: 107
<212> TYPE: PRT
<213> ORGANISM: Artificial Sequence
<220> FEATURE:
<223> OTHER INFORMATION: Light chain variable region

<400> SEQUENCE: 12

Glu Ile Val Met Thr Gln Ser Pro Ala Thr Leu Ser Leu Ser Val Gly
1               5                   10                  15

Glu Arg Val Thr Leu Ser Cys Lys Ala Ser Glu Asn Val Gly Gly Tyr
            20                  25                  30

Val Ser Trp Tyr Gln Gln Lys Pro Asp Gln Ser Pro Lys Leu Leu Ile
        35                  40                  45

Tyr Gly Ala Ser Ser Arg His Thr Gly Val Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr His Cys Gly Gln Asn Tyr Ile Tyr Pro Phe
                85                  90                  95
```

```
Thr Phe Gly Gly Gly Thr Lys Leu Glu Ile Lys
            100                 105


<210> SEQ ID NO 13
<211> LENGTH: 107
<212> TYPE: PRT
<213> ORGANISM: Artificial Sequence
<220> FEATURE:
<223> OTHER INFORMATION: Light chain variable region

<400> SEQUENCE: 13

Glu Ile Val Leu Thr Gln Ser Pro Ala Thr Leu Ser Leu Ser Pro Gly
1               5                   10                  15

Glu Arg Ala Thr Leu Ser Cys Lys Ala Ser Glu Asn Val Gly Gly Tyr
            20                  25                  30

Val Ser Trp Tyr Gln Gln Lys Pro Asp Gln Ser Pro Lys Leu Leu Ile
        35                  40                  45

Tyr Gly Ala Ser Ser Arg His Thr Gly Val Pro Asp Arg Phe Thr Gly
    50                  55                  60

Ser Gly Ser Glu Thr Asp Phe Thr Leu Thr Ile Ser Ser Val Gln Ala
65                  70                  75                  80

Glu Asp Leu Ala Ala Tyr His Cys Gly Gln Asn Tyr Ile Tyr Pro Phe
                85                  90                  95

Thr Phe Gly Gly Gly Thr Lys Leu Glu Ile Lys
            100                 105


<210> SEQ ID NO 14
<211> LENGTH: 107
<212> TYPE: PRT
<213> ORGANISM: Artificial Sequence
<220> FEATURE:
<223> OTHER INFORMATION: Full-length sequence of antibody constant
      region

<400> SEQUENCE: 14

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 15
<211> LENGTH: 326
<212> TYPE: PRT
<213> ORGANISM: Artificial Sequence
<220> FEATURE:
<223> OTHER INFORMATION: Full-length sequence of antibody constant
      region

<400> SEQUENCE: 15

Ala Ser Thr Lys Gly Pro Ser Val Phe Pro Leu Ala Pro Cys Ser Arg
1               5                   10                  15
```

```
Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Ala Ala Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Lys Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly
                325
```

<210> SEQ ID NO 16
<211> LENGTH: 229
<212> TYPE: PRT
<213> ORGANISM: Artificial Sequence
<220> FEATURE:
<223> OTHER INFORMATION: Human IgG4 wild type Fc sequence

<400> SEQUENCE: 16

```
Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45
```

```
Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225
```

<210> SEQ ID NO 17
<211> LENGTH: 442
<212> TYPE: PRT
<213> ORGANISM: Artificial Sequence
<220> FEATURE:
<223> OTHER INFORMATION: Heavy chain

<400> SEQUENCE: 17

```
Glu Val Gln Leu Leu Glu Ser Gly Gly Gly Leu Val Gln Pro Gly Gly
1               5                   10                  15

Ser Leu Lys Leu Ser Cys Lys Ala Ser Gly Tyr Ala Phe Thr Asn Tyr
            20                  25                  30

Trp Leu Gly Trp Met Lys Gln Arg Pro Gly His Gly Leu Glu Trp Ile
        35                  40                  45

Gly Asp Phe Tyr Pro Arg Thr Gly Asn Thr Phe Tyr Asn Glu Asn Phe
    50                  55                  60

Lys Gly Lys Val Thr Leu Thr Ala Asp Lys Ser Ser Asn Thr Ala Tyr
65                  70                  75                  80

Met Gln Leu Ser Ser Leu Thr Ser Glu Asp Ser Ala Val Tyr Leu Cys
                85                  90                  95

Ala Arg Ala Gly Thr Gly Phe Asp Tyr Trp Gly Gln Gly Thr Thr Leu
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175
```

```
Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
        195                 200                 205

Lys Val Asp Lys Arg Val Glu Ser Lys Tyr Gly Pro Pro Cys Pro Pro
    210                 215                 220

Cys Pro Ala Pro Glu Ala Ala Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Glu Gly
                405                 410                 415

Asn Val Phe Ser Cys Ser Val Met His Glu Ala Leu His Asn His Tyr
            420                 425                 430

Thr Gln Lys Ser Leu Ser Leu Ser Leu Gly
        435                 440
```

<210> SEQ ID NO 18
<211> LENGTH: 442
<212> TYPE: PRT
<213> ORGANISM: Artificial Sequence
<220> FEATURE:
<223> OTHER INFORMATION: Heavy chain

<400> SEQUENCE: 18

```
Glu Val Gln Leu Leu Glu Ser Gly Gly Gly Leu Val Gln Pro Gly Gly
1               5                   10                  15

Ser Leu Lys Leu Ser Cys Lys Ala Ser Gly Tyr Ala Phe Thr Asn Tyr
            20                  25                  30

Trp Leu Gly Trp Met Lys Gln Arg Pro Gly His Gly Leu Glu Trp Ile
        35                  40                  45

Gly Gly Phe Tyr Pro Arg Thr Gly Asn Thr Phe Tyr Asn Glu Asn Phe
    50                  55                  60

Lys Gly Lys Val Thr Leu Thr Ala Asp Lys Ser Ser Asn Thr Ala Tyr
65                  70                  75                  80

Met Gln Leu Ser Ser Leu Thr Ser Glu Asp Ser Ala Val Tyr Leu Cys
                85                  90                  95
```

```
Ala Arg Ala Gly Thr Gly Phe Asp Tyr Trp Gly Gln Gly Thr Thr Leu
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
        195                 200                 205

Lys Val Asp Lys Arg Val Glu Ser Lys Tyr Gly Pro Pro Cys Pro Pro
    210                 215                 220

Cys Pro Ala Pro Glu Ala Ala Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Glu Gly
                405                 410                 415

Asn Val Phe Ser Cys Ser Val Met His Glu Ala Leu His Asn His Tyr
            420                 425                 430

Thr Gln Lys Ser Leu Ser Leu Ser Leu Gly
        435                 440


<210> SEQ ID NO 19
<211> LENGTH: 442
<212> TYPE: PRT
<213> ORGANISM: Artificial Sequence
<220> FEATURE:
<223> OTHER INFORMATION: Heavy chain

<400> SEQUENCE: 19

Glu Val Gln Leu Leu Glu Ser Gly Gly Gly Leu Val Gln Pro Gly Gly
1               5                   10                  15
```

-continued

```
Ser Leu Lys Leu Ser Cys Lys Ala Ser Gly Tyr Ala Phe Thr Asn Tyr
            20                  25                  30

Trp Leu Gly Trp Met Lys Gln Arg Pro Gly His Gly Leu Glu Trp Ile
        35                  40                  45

Gly Asp Phe Tyr Pro Arg Thr Gly Asn Thr Phe Tyr Asn Glu Asn Phe
    50                  55                  60

Lys Gly Gln Val Thr Met Ser Val Asp Lys Ser Ile Thr Thr Ala Tyr
65                  70                  75                  80

Leu Gln Trp Asn Ser Leu Lys Ala Ser Asp Thr Ala Met Tyr Tyr Cys
                85                  90                  95

Ala Arg Ala Gly Thr Gly Phe Asp Tyr Trp Gly Gln Gly Thr Thr Leu
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
        195                 200                 205

Lys Val Asp Lys Arg Val Glu Ser Lys Tyr Gly Pro Pro Cys Pro Pro
    210                 215                 220

Cys Pro Ala Pro Glu Ala Ala Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Glu Gly
                405                 410                 415

Asn Val Phe Ser Cys Ser Val Met His Glu Ala Leu His Asn His Tyr
            420                 425                 430
```

```
Thr Gln Lys Ser Leu Ser Leu Ser Leu Gly
        435                 440


<210> SEQ ID NO 20
<211> LENGTH: 442
<212> TYPE: PRT
<213> ORGANISM: Artificial Sequence
<220> FEATURE:
<223> OTHER INFORMATION: Heavy chain

<400> SEQUENCE: 20

Gln Val Gln Leu Val Gln Ser Gly Val Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Trp Leu Gly Trp Met Lys Gln Arg Pro Gly His Gly Leu Glu Trp Ile
        35                  40                  45

Gly Asp Phe Tyr Pro Arg Thr Gly Asn Thr Phe Tyr Asn Glu Asn Phe
    50                  55                  60

Lys Gly Gln Val Thr Met Ser Val Asp Lys Ser Ile Thr Thr Ala Tyr
65                  70                  75                  80

Leu Gln Trp Asn Ser Leu Lys Ala Ser Asp Thr Ala Met Tyr Tyr Cys
                85                  90                  95

Ala Arg Ala Gly Thr Gly Phe Asp Tyr Trp Gly Gln Gly Thr Thr Leu
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
        195                 200                 205

Lys Val Asp Lys Arg Val Glu Ser Lys Tyr Gly Pro Pro Cys Pro Pro
    210                 215                 220

Cys Pro Ala Pro Glu Ala Ala Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
            340                 345                 350
```

```
Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Glu Gly
                405                 410                 415

Asn Val Phe Ser Cys Ser Val Met His Glu Ala Leu His Asn His Tyr
            420                 425                 430

Thr Gln Lys Ser Leu Ser Leu Ser Leu Gly
        435                 440


<210> SEQ ID NO 21
<211> LENGTH: 442
<212> TYPE: PRT
<213> ORGANISM: Artificial Sequence
<220> FEATURE:
<223> OTHER INFORMATION: Heavy chain

<400> SEQUENCE: 21

Gln Val Gln Leu Val Gln Ser Gly Val Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Trp Leu Gly Trp Met Lys Gln Arg Pro Gly His Gly Leu Glu Trp Ile
        35                  40                  45

Gly Asp Phe Tyr Pro Arg Thr Gly Asn Thr Phe Tyr Asn Glu Asn Phe
    50                  55                  60

Lys Gly Lys Val Thr Ile Thr Ala Asp Lys Ser Ile Thr Thr Ala Tyr
65                  70                  75                  80

Met Gln Leu Ser Ser Leu Lys Ala Ser Asp Thr Ala Val Tyr Tyr Cys
                85                  90                  95

Ala Arg Ala Gly Thr Gly Phe Asp Tyr Trp Gly Gln Gly Thr Thr Leu
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
        195                 200                 205

Lys Val Asp Lys Arg Val Glu Ser Lys Tyr Gly Pro Pro Cys Pro Pro
    210                 215                 220

Cys Pro Ala Pro Glu Ala Ala Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
            260                 265                 270
```

```
Trp Tyr Val Asp Gly Val Glu Val His Asn Ala Lys Thr Lys Pro Arg
        275                 280                 285

Glu Glu Gln Phe Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Glu Gly
                405                 410                 415

Asn Val Phe Ser Cys Ser Val Met His Glu Ala Leu His Asn His Tyr
            420                 425                 430

Thr Gln Lys Ser Leu Ser Leu Ser Leu Gly
        435                 440


<210> SEQ ID NO 22
<211> LENGTH: 442
<212> TYPE: PRT
<213> ORGANISM: Artificial Sequence
<220> FEATURE:
<223> OTHER INFORMATION: Heavy chain

<400> SEQUENCE: 22

Gln Val Gln Leu Val Gln Ser Gly Val Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Trp Leu Gly Trp Val Lys Gln Arg Pro Gly His Gly Leu Glu Trp Ile
        35                  40                  45

Gly Asp Phe Tyr Pro Arg Thr Gly Asn Thr Phe Tyr Asn Glu Asn Phe
    50                  55                  60

Lys Gly Lys Val Thr Ile Thr Ala Asp Lys Ser Ile Thr Thr Ala Tyr
65                  70                  75                  80

Met Gln Leu Ser Ser Leu Lys Ala Ser Asp Thr Ala Val Tyr Tyr Cys
                85                  90                  95

Ala Arg Ala Gly Thr Gly Phe Asp Tyr Trp Gly Gln Gly Thr Thr Leu
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190
```

```
Gly Thr Lys Thr Tyr Thr Cys Asn Val Asp His Lys Pro Ser Asn Thr
        195                 200                 205

Lys Val Asp Lys Arg Val Glu Ser Lys Tyr Gly Pro Pro Cys Pro Pro
    210                 215                 220

Cys Pro Ala Pro Glu Ala Ala Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Glu Gly
                405                 410                 415

Asn Val Phe Ser Cys Ser Val Met His Glu Ala Leu His Asn His Tyr
            420                 425                 430

Thr Gln Lys Ser Leu Ser Leu Ser Leu Gly
        435                 440


<210> SEQ ID NO 23
<211> LENGTH: 442
<212> TYPE: PRT
<213> ORGANISM: Artificial Sequence
<220> FEATURE:
<223> OTHER INFORMATION: Heavy chain

<400> SEQUENCE: 23

Gln Val Gln Leu Val Gln Ser Gly Val Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Trp Leu Gly Trp Met Lys Gln Arg Pro Gly His Gly Leu Glu Trp Ile
        35                  40                  45

Gly Asp Phe Tyr Pro Arg Thr Gly Asn Thr Phe Tyr Asn Glu Asn Phe
    50                  55                  60

Lys Gly Lys Val Thr Leu Thr Ala Asp Lys Ser Ser Asn Thr Ala Tyr
65                  70                  75                  80

Met Gln Leu Ser Ser Leu Thr Ser Glu Asp Ser Ala Val Tyr Leu Cys
                85                  90                  95

Ala Arg Ala Gly Thr Gly Phe Asp Tyr Trp Gly Gln Gly Thr Thr Leu
            100                 105                 110
```

```
Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
        195                 200                 205

Lys Val Asp Lys Arg Val Glu Ser Lys Tyr Gly Pro Pro Cys Pro Pro
    210                 215                 220

Cys Pro Ala Pro Glu Ala Ala Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Glu Gly
                405                 410                 415

Asn Val Phe Ser Cys Ser Val Met His Glu Ala Leu His Asn His Tyr
            420                 425                 430

Thr Gln Lys Ser Leu Ser Leu Ser Leu Gly
        435                 440
```

<210> SEQ ID NO 24
<211> LENGTH: 214
<212> TYPE: PRT
<213> ORGANISM: Artificial Sequence
<220> FEATURE:
<223> OTHER INFORMATION: Light chain

<400> SEQUENCE: 24

```
Glu Ile Val Met Thr Gln Ser Pro Ala Thr Leu Ser Leu Ser Val Gly
1               5                   10                  15

Glu Arg Val Thr Leu Ser Cys Lys Ala Ser Glu Asn Val Gly Gly Tyr
            20                  25                  30
```

```
Val Ser Trp Tyr Gln Gln Lys Pro Asp Gln Ser Pro Lys Leu Leu Ile
        35                  40                  45

Tyr Gly Ala Ser Ser Arg His Thr Gly Val Pro Asp Arg Phe Thr Gly
    50                  55                  60

Ser Gly Ser Glu Thr Asp Phe Thr Leu Thr Ile Ser Ser Val Gln Ala
65                  70                  75                  80

Glu Asp Leu Ala Ala Tyr His Cys Gly Gln Asn Tyr Ile Tyr Pro Phe
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 25
<211> LENGTH: 214
<212> TYPE: PRT
<213> ORGANISM: Artificial Sequence
<220> FEATURE:
<223> OTHER INFORMATION: Light chain

<400> SEQUENCE: 25

Glu Ile Val Met Thr Gln Ser Pro Ala Thr Leu Ser Leu Ser Val Gly
1               5                   10                  15

Glu Arg Val Thr Leu Ser Cys Lys Ala Ser Glu Asn Val Gly Gly Tyr
            20                  25                  30

Val Ser Trp Tyr Gln Gln Lys Pro Asp Gln Ser Pro Lys Leu Leu Ile
        35                  40                  45

Tyr Gly Ala Ser Ser Arg Ala Thr Gly Val Pro Asp Arg Phe Thr Gly
    50                  55                  60

Ser Gly Ser Glu Thr Asp Phe Thr Leu Thr Ile Ser Ser Val Gln Ala
65                  70                  75                  80

Glu Asp Leu Ala Ala Tyr His Cys Gly Gln Asn Tyr Ile Tyr Pro Phe
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175
```

```
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 26
<211> LENGTH: 214
<212> TYPE: PRT
<213> ORGANISM: Artificial Sequence
<220> FEATURE:
<223> OTHER INFORMATION: Light chain

<400> SEQUENCE: 26

Glu Ile Val Met Thr Gln Ser Pro Ala Thr Leu Ser Leu Ser Val Gly
1               5                   10                  15

Glu Arg Val Thr Leu Ser Cys Lys Ala Ser Glu Asn Val Gly Gly Tyr
            20                  25                  30

Val Ser Trp Tyr Gln Gln Lys Pro Asp Gln Ser Pro Lys Leu Leu Ile
        35                  40                  45

Tyr Gly Ala Ser Ser Arg His Thr Gly Val Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr His Cys Gly Gln Asn Tyr Ile Tyr Pro Phe
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 27
<211> LENGTH: 214
<212> TYPE: PRT
<213> ORGANISM: Artificial Sequence
<220> FEATURE:
<223> OTHER INFORMATION: Light chain

<400> SEQUENCE: 27

Glu Ile Val Leu Thr Gln Ser Pro Ala Thr Leu Ser Leu Ser Pro Gly
1               5                   10                  15

Glu Arg Ala Thr Leu Ser Cys Lys Ala Ser Glu Asn Val Gly Gly Tyr
            20                  25                  30

Val Ser Trp Tyr Gln Gln Lys Pro Asp Gln Ser Pro Lys Leu Leu Ile
        35                  40                  45
```

```
Tyr Gly Ala Ser Ser Arg His Thr Gly Val Pro Asp Arg Phe Thr Gly
    50                  55                  60

Ser Gly Ser Glu Thr Asp Phe Thr Leu Thr Ile Ser Ser Val Gln Ala
65                  70                  75                  80

Glu Asp Leu Ala Ala Tyr His Cys Gly Gln Asn Tyr Ile Tyr Pro Phe
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 28
<211> LENGTH: 442
<212> TYPE: PRT
<213> ORGANISM: Artificial Sequence
<220> FEATURE:
<223> OTHER INFORMATION: Heavy chain

<400> SEQUENCE: 28

Gln Val Gln Leu Gln Gln Ser Gly Ala Glu Leu Val Arg Pro Gly Thr
1               5                   10                  15

Ser Val Lys Ile Ser Cys Lys Ala Ser Gly Tyr Ala Phe Thr Asn Tyr
            20                  25                  30

Trp Leu Gly Trp Met Lys Gln Arg Pro Gly His Gly Leu Glu Trp Ile
        35                  40                  45

Gly Asp Phe Tyr Pro Arg Thr Gly Asn Thr Phe Tyr Asn Glu Asn Phe
    50                  55                  60

Lys Gly Lys Val Thr Leu Thr Ala Asp Lys Ser Ser Asn Thr Ala Tyr
65                  70                  75                  80

Met Gln Leu Ser Ser Leu Thr Ser Glu Asp Ser Ala Val Tyr Leu Cys
                85                  90                  95

Ala Arg Ala Gly Thr Gly Phe Asp Tyr Trp Gly Gln Gly Thr Thr Leu
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190
```

```
Gly Thr Lys Thr Tyr Thr Cys Asn Val Asp His Lys Pro Ser Asn Thr
        195                 200                 205

Lys Val Asp Lys Arg Val Glu Ser Lys Tyr Gly Pro Pro Cys Pro Pro
    210                 215                 220

Cys Pro Ala Pro Glu Ala Ala Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Glu Gly
                405                 410                 415

Asn Val Phe Ser Cys Ser Val Met His Glu Ala Leu His Asn His Tyr
            420                 425                 430

Thr Gln Lys Ser Leu Ser Leu Ser Leu Gly
        435                 440


<210> SEQ ID NO 29
<211> LENGTH: 214
<212> TYPE: PRT
<213> ORGANISM: Artificial Sequence
<220> FEATURE:
<223> OTHER INFORMATION: Light chain

<400> SEQUENCE: 29

Ser Ile Val Met Thr Gln Ser Pro Lys Ser Met Ser Met Ser Val Gly
1               5                   10                  15

Glu Arg Val Thr Leu Ser Cys Lys Ala Ser Glu Asn Val Gly Gly Tyr
            20                  25                  30

Val Ser Trp Tyr Gln Gln Lys Pro Asp Gln Ser Pro Lys Leu Leu Ile
        35                  40                  45

Tyr Gly Ala Ser Ser Arg His Thr Gly Val Pro Asp Arg Phe Thr Gly
    50                  55                  60

Ser Gly Ser Glu Thr Asp Phe Thr Leu Thr Ile Ser Ser Val Gln Ala
65                  70                  75                  80

Glu Asp Leu Ala Ala Tyr His Cys Gly Gln Asn Tyr Ile Tyr Pro Phe
                85                  90                  95

Thr Phe Gly Gly Gly Thr Lys Leu Glu Ile Lys Arg Thr Val Ala Ala
            100                 105                 110
```

```
Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 30
<211> LENGTH: 1326
<212> TYPE: DNA
<213> ORGANISM: Artificial Sequence
<220> FEATURE:
<223> OTHER INFORMATION: Nucleic acid molecule

<400> SEQUENCE: 30

```
gaggtgcagc tgctggagtc tggaggagga ctggtgcagc caggaggctc tctgaagctg     60

tcctgcaagg ccagcggcta cgctttcacc aactattggc tgggatggat gaagcagagg    120

ccaggacacg gactggagtg gatcggcgac ttttaccctc ggaccggcaa cacattctat    180

aacgagaact tcaagggcaa ggtgaccctg acagccgata agtccagcaa taccgcttac    240

atgcagctgt cttccctgac atccgaggac tccgccgtgt acctgtgcgc tagggctgga    300

accggattcg attattgggg ccagggcacc acactgacag tgagctctgc cagcaccaag    360

ggccccagcg tgttccctct ggctccttgt agccggtcca cctccgagtc cacagctgct    420

ctgggctgcc tcgtgaagga ctactttccc gaacccgtta ccgtgagctg gaatagcggc    480

gctttaacct ccggagtgca caccttcccc gctgtgctcc agtcctccgg tttatactct    540

ttatcctccg tggtgaccgt gccttcctcc agcctcggca ccaagaccta cacttgtaac    600

gtggaccaca agcccagcaa caccaaggtg gacaagaggg tggagtccaa gtacggacct    660

ccttgtcccc cttgccccgc ccccgaggcc gctggcggac cctccgtgtt cctcttcccc    720

cccaaaccca aggacacttt aatgatctcc cggacccccg aagtgacttg tgtggtggtg    780

gacgtgtccc aagaagaccc cgaggtgcag tttaactggt acgtggatgg cgtggaggtg    840

cacaacgcca agaccaagcc tagggaggaa cagttcaact ccacctaccg ggtggtgtcc    900

gtgctcaccg tgctgcatca agattggctg aacggcaagg agtacaagtg caaggtgagc    960

aacaagggac tgcccagctc catcgagaag accatcagca aggccaaagg ccagccccgg   1020

gaacctcaag tttatacact gccccccagc caagaagaga tgaccaagaa ccaagtttct   1080

ttaacttgtt tagtgaaggg cttctaccct agcgacatcg ctgtggagtg ggagtccaat   1140

ggccagcccg aaaacaatta taagaccacc ccccccgtgc tggactccga tggttctttt   1200

tttttatact ccaagctgac agtggacaag tctcgttggc aagaaggcaa cgtgttctct   1260

tgtagcgtga tgcacgaggc tttacacaac cactacaccc agaagtcttt atctctgtct   1320

ttaggc                                                              1326
```

<210> SEQ ID NO 31
<211> LENGTH: 1326
<212> TYPE: DNA
<213> ORGANISM: Artificial Sequence
<220> FEATURE:
<223> OTHER INFORMATION: Nucleic acid molecule

<400> SEQUENCE: 31
gaggtgcagc tgctggagag cggcggcggc ctggtgcagc ccggcggcag cctgaagctg 60
agctgcaagg ccagcggcta cgccttcacc aactactggc tgggctggat gaagcagagg 120
cccggccacg gcctggagtg gatcggcggc ttctacccca ggaccggcaa caccttctac 180
aacgagaact tcaagggcaa ggtgaccctg accgccgaca agagcagcaa caccgcctac 240
atgcagctga gcagcctgac cagcgaggac agcgccgtgt acctgtgcgc cagggccggc 300
accggcttcg actactgggg ccagggcacc accctgaccg tgagcagcgc cagcaccaag 360
ggccccagcg tgttccctct ggctccttgt agccggtcca cctccgagtc cacagctgct 420
ctgggctgcc tcgtgaagga ctactttccc gaacccgtta ccgtgagctg gaatagcggc 480
gctttaacct ccggagtgca caccttcccc gctgtgctcc agtcctccgg tttatactct 540
ttatcctccg tggtgaccgt gccttcctcc agcctcggca ccaagaccta cacttgtaac 600
gtggaccaca agcccagcaa caccaaggtg gacaagaggg tggagtccaa gtacggacct 660
ccttgtcccc cttgccccgc ccccgaggcc gctggcggac cctccgtgtt cctcttcccc 720
cccaaaccca aggacacttt aatgatctcc cggacccccg aagtgacttg tgtggtggtg 780
gacgtgtccc aagaagaccc cgaggtgcag tttaactggt acgtggatgg cgtggaggtg 840
cacaacgcca agaccaagcc tagggaggaa cagttcaact ccacctaccg ggtggtgtcc 900
gtgctcaccg tgctgcatca agattggctg aacggcaagg agtacaagtg caaggtgagc 960
aacaagggac tgcccagctc catcgagaag accatcagca aggccaaagg ccagccccgg 1020
gaacctcaag tttatacact gccccccagc caagaagaga tgaccaagaa ccaagtttct 1080
ttaacttgtt tagtgaaggg cttctaccct agcgacatcg ctgtggagtg ggagtccaat 1140
ggccagcccg aaaacaatta taagaccacc ccccccgtgc tggactccga tggttctttt 1200
tttttatact ccaagctgac agtggacaag tctcgttggc aagaaggcaa cgtgttctct 1260
tgtagcgtga tgcacgaggc tttacacaac cactacaccc agaagtcttt atctctgtct 1320
ttaggc 1326

<210> SEQ ID NO 32
<211> LENGTH: 1326
<212> TYPE: DNA
<213> ORGANISM: Artificial Sequence
<220> FEATURE:
<223> OTHER INFORMATION: Nucleic acid molecule

<400> SEQUENCE: 32
gaggtgcagc tgctggagtc cggaggagga ctggtgcagc caggaggctc tctgaagctg 60
tcctgcaagg ccagcggcta cgctttcacc aactattggc tgggatggat gaagcagagg 120
ccaggacacg gactggagtg gatcggcgac ttttaccctc ggaccggcaa tacattctat 180
aacgagaact tcaagggcca ggtgacaatg tctgtggata agtccatcac cacagcctac 240
ctgcagtgga acagcctgaa ggcctctgac accgctatgt actattgtgc cagggctggc 300
acaggcttcg attattgggg ccagggcacc acactgaccg tgtccagcgc cagcaccaag 360
ggccccagcg tgttccctct ggctccttgt agccggtcca cctccgagtc cacagctgct 420

```
ctgggctgcc tcgtgaagga ctactttccc gaacccgtta ccgtgagctg gaatagcggc    480

gctttaacct ccggagtgca caccttcccc gctgtgctcc agtcctccgg tttatactct    540

ttatcctccg tggtgaccgt gccttcctcc agcctcggca ccaagaccta cacttgtaac    600

gtggaccaca agcccagcaa caccaaggtg gacaagaggg tggagtccaa gtacggacct    660

ccttgtcccc cttgccccgc cccccgaggcc gctggcggac cctccgtgtt cctcttcccc    720

cccaaaccca aggacacttt aatgatctcc cggacccccg aagtgacttg tgtggtggtg    780

gacgtgtccc aagaagaccc cgaggtgcag tttaactggt acgtggatgg cgtggaggtg    840

cacaacgcca agaccaagcc tagggaggaa cagttcaact ccacctaccg ggtggtgtcc    900

gtgctcaccg tgctgcatca agattggctg aacggcaagg agtacaagtg caaggtgagc    960

aacaagggac tgcccagctc catcgagaag accatcagca aggccaaagg ccagccccgg   1020

gaacctcaag tttatacact gccccccagc caagaagaga tgaccaagaa ccaagtttct   1080

ttaacttgtt tagtgaaggg cttctaccct agcgacatcg ctgtggagtg ggagtccaat   1140

ggccagcccg aaaacaatta taagaccacc ccccccgtgc tggactccga tggttctttt   1200

tttttatact ccaagctgac agtggacaag tctcgttggc aagaaggcaa cgtgttctct   1260

tgtagcgtga tgcacgaggc tttacacaac cactacaccc agaagtcttt atctctgtct   1320

ttaggc                                                              1326
```

```
<210> SEQ ID NO 33
<211> LENGTH: 1326
<212> TYPE: DNA
<213> ORGANISM: Artificial Sequence
<220> FEATURE:
<223> OTHER INFORMATION: Nucleic acid molecule

<400> SEQUENCE: 33

caagtgcaac tggttcaatc tggagtggaa gttaagaagc ctggtgccag cgttaaagtg     60

agttgcaaag ccagcggata tgcctttacc aactattggc tgggctggat gaaacagagg    120

cctggccatg gtctggaatg gatcggagac ttttatccac gcaccggcaa cacattctat    180

aacgagaact tcaaaggtca ggtgaccatg tccgtggata agagcatcac taccgcttac    240

ctccagtgga acagtctgaa ggcttctgac accgccatgt actactgcgc tagggcaggc    300

accgggttcg actactgggg tcaagggacc accctcaccg tgagtagcgc cagcaccaag    360

ggccccagcg tgttccctct ggctccttgt agccggtcca cctccgagtc cacagctgct    420

ctgggctgcc tcgtgaagga ctactttccc gaacccgtta ccgtgagctg gaatagcggc    480

gctttaacct ccggagtgca caccttcccc gctgtgctcc agtcctccgg tttatactct    540

ttatcctccg tggtgaccgt gccttcctcc agcctcggca ccaagaccta cacttgtaac    600

gtggaccaca agcccagcaa caccaaggtg gacaagaggg tggagtccaa gtacggacct    660

ccttgtcccc cttgccccgc cccccgaggcc gctggcggac cctccgtgtt cctcttcccc    720

cccaaaccca aggacacttt aatgatctcc cggacccccg aagtgacttg tgtggtggtg    780

gacgtgtccc aagaagaccc cgaggtgcag tttaactggt acgtggatgg cgtggaggtg    840

cacaacgcca agaccaagcc tagggaggaa cagttcaact ccacctaccg ggtggtgtcc    900

gtgctcaccg tgctgcatca agattggctg aacggcaagg agtacaagtg caaggtgagc    960

aacaagggac tgcccagctc catcgagaag accatcagca aggccaaagg ccagccccgg   1020

gaacctcaag tttatacact gccccccagc caagaagaga tgaccaagaa ccaagtttct   1080

ttaacttgtt tagtgaaggg cttctaccct agcgacatcg ctgtggagtg ggagtccaat   1140
```

```
ggccagcccg aaaacaatta taagaccacc ccccccgtgc tggactccga tggttctttt   1200

tttttatact ccaagctgac agtggacaag tctcgttggc aagaaggcaa cgtgttctct   1260

tgtagcgtga tgcacgaggc tttacacaac cactacaccc agaagtcttt atctctgtct   1320

ttaggc                                                              1326
```

<210> SEQ ID NO 34
<211> LENGTH: 1326
<212> TYPE: DNA
<213> ORGANISM: Artificial Sequence
<220> FEATURE:
<223> OTHER INFORMATION: Nucleic acid molecule

<400> SEQUENCE: 34

```
caagtgcagc tggttcaaag tggtgttgaa gttaagaagc ctggagctag tgtgaaggtg     60

tcctgtaagg cctccggcta tgcctttaca aactactggc tcgggtggat gaagcagcgc    120

ccaggacacg gtctggaatg gattggcgac ttttacccac ggacaggaaa tacattctat    180

aatgaaaact tcaaaggcaa agtgaccatc acagccgata agtccattac cactgcatac    240

atgcagctca gtagtctcaa agctagtgat acagcagtgt attactgcgc cagggccggc    300

accgggttcg actactgggg gcagggaacc accctcaccg tgagctctgc cagcaccaag    360

ggccccagcg tgttccctct ggctccttgt agccggtcca cctccgagtc cacagctgct    420

ctgggctgcc tcgtgaagga ctactttccc gaacccgtta ccgtgagctg gaatagcggc    480

gctttaacct ccggagtgca caccttcccc gctgtgctcc agtcctccgg tttatactct    540

ttatcctccg tggtgaccgt gccttcctcc agcctcggca ccaagaccta cacttgtaac    600

gtggaccaca agcccagcaa caccaaggtg gacaagaggg tggagtccaa gtacggacct    660

ccttgtcccc cttgccccgc ccccgaggcc gctggcggac cctccgtgtt cctcttcccc    720

cccaaaccca aggacacttt aatgatctcc cggacccccg aagtgacttg tgtggtggtg    780

gacgtgtccc aagaagaccc cgaggtgcag tttaactggt acgtggatgg cgtggaggtg    840

cacaacgcca agaccaagcc tagggaggaa cagttcaact ccacctaccg ggtggtgtcc    900

gtgctcaccg tgctgcatca agattggctg aacggcaagg agtacaagtg caaggtgagc    960

aacaagggac tgcccagctc catcgagaag accatcagca aggccaaagg ccagccccgg   1020

gaacctcaag tttatacact gcccccccagc caagaagaga tgaccaagaa ccaagtttct   1080

ttaacttgtt tagtgaaggg cttctaccct agcgacatcg ctgtggagtg ggagtccaat   1140

ggccagcccg aaaacaatta taagaccacc ccccccgtgc tggactccga tggttctttt   1200

tttttatact ccaagctgac agtggacaag tctcgttggc aagaaggcaa cgtgttctct   1260

tgtagcgtga tgcacgaggc tttacacaac cactacaccc agaagtcttt atctctgtct   1320

ttaggc                                                              1326
```

<210> SEQ ID NO 35
<211> LENGTH: 1326
<212> TYPE: DNA
<213> ORGANISM: Artificial Sequence
<220> FEATURE:
<223> OTHER INFORMATION: Nucleic acid molecule

<400> SEQUENCE: 35

```
caagtccaac tggttcaatc tggcgtggaa gtcaagaagc ccggagcctc cgtgaaggtg     60

agctgcaagg caagcggcta tgcattcact aactactggc tcggatgggt gaaacaacgg    120
```

```
ccaggacatg gcctggaatg gatcggcgac ttctacccta ggactggcaa cactttctat    180

aacgagaact ttaagggcaa ggtcaccatt acagctgata agagtatcac taccgcctac    240

atgcagctgt cttccctgaa agctagtgat acagccgttt attactgtgc tcgggctggc    300

acaggattcg attattgggg acagggtacc acactcacag tgtcctctgc cagcaccaag    360

ggccccagcg tgttccctct ggctccttgt agccggtcca cctccgagtc cacagctgct    420

ctgggctgcc tcgtgaagga ctactttccc gaacccgtta ccgtgagctg gaatagcggc    480

gctttaacct ccggagtgca caccttcccc gctgtgctcc agtcctccgg tttatactct    540

ttatcctccg tggtgaccgt gccttcctcc agcctcggca ccaagaccta cacttgtaac    600

gtggaccaca agcccagcaa caccaaggtg gacaagaggg tggagtccaa gtacggacct    660

ccttgtcccc cttgccccgc ccccgaggcc gctggcggac cctccgtgtt cctcttcccc    720

cccaaaccca aggacacttt aatgatctcc cggacccccg aagtgacttg tgtggtggtg    780

gacgtgtccc aagaagaccc cgaggtgcag tttaactggt acgtggatgg cgtggaggtg    840

cacaacgcca agaccaagcc tagggaggaa cagttcaact ccacctaccg ggtggtgtcc    900

gtgctcaccg tgctgcatca agattggctg aacggcaagg agtacaagtg caaggtgagc    960

aacaagggac tgcccagctc catcgagaag accatcagca aggccaaagg ccagccccgg   1020

gaacctcaag tttatacact gccccccagc caagaagaga tgaccaagaa ccaagtttct   1080

ttaacttgtt tagtgaaggg cttctaccct agcgacatcg ctgtggagtg ggagtccaat   1140

ggccagcccg aaaacaatta taagaccacc ccccccgtgc tggactccga tggttctttt   1200

tttttatact ccaagctgac agtggacaag tctcgttggc aagaaggcaa cgtgttctct   1260

tgtagcgtga tgcacgaggc tttacacaac cactacaccc agaagtcttt atctctgtct   1320

ttaggc                                                              1326
```

<210> SEQ ID NO 36
<211> LENGTH: 1326
<212> TYPE: DNA
<213> ORGANISM: Artificial Sequence
<220> FEATURE:
<223> OTHER INFORMATION: Nucleic acid molecule

<400> SEQUENCE: 36

```
caagttcagc tggtgcaatc cggtgtcgag gtgaagaaac caggcgcaag cgtgaaagtc     60

tcctgcaagg cttctggcta tgccttcact aactactggc tcggctggat gaagcagagg    120

cccggacatg ggctggagtg gatcggagac ttctatccca gaactggaaa caccttttac    180

aacgagaatt tcaagggcaa ggtcaccctg actgccgaca aatcctctaa cacagcttac    240

atgcagctga gcagtctgac atccgaagac tctgcagttt acctgtgtgc tcgggcaggc    300

acaggcttcg attattgggg gcaagggacc actctgactg tgtcttccgc cagcaccaag    360

ggccccagcg tgttccctct ggctccttgt agccggtcca cctccgagtc cacagctgct    420

ctgggctgcc tcgtgaagga ctactttccc gaacccgtta ccgtgagctg gaatagcggc    480

gctttaacct ccggagtgca caccttcccc gctgtgctcc agtcctccgg tttatactct    540

ttatcctccg tggtgaccgt gccttcctcc agcctcggca ccaagaccta cacttgtaac    600

gtggaccaca agcccagcaa caccaaggtg gacaagaggg tggagtccaa gtacggacct    660

ccttgtcccc cttgccccgc ccccgaggcc gctggcggac cctccgtgtt cctcttcccc    720

cccaaaccca aggacacttt aatgatctcc cggacccccg aagtgacttg tgtggtggtg    780

gacgtgtccc aagaagaccc cgaggtgcag tttaactggt acgtggatgg cgtggaggtg    840
```

```
cacaacgcca agaccaagcc tagggaggaa cagttcaact ccacctaccg ggtggtgtcc    900

gtgctcaccg tgctgcatca agattggctg aacggcaagg agtacaagtg caaggtgagc    960

aacaagggac tgcccagctc catcgagaag accatcagca aggccaaagg ccagccccgg   1020

gaacctcaag tttatacact gccccccagc caagaagaga tgaccaagaa ccaagtttct   1080

ttaacttgtt tagtgaaggg cttctaccct agcgacatcg ctgtggagtg ggagtccaat   1140

ggccagcccg aaaacaatta taagaccacc ccccccgtgc tggactccga tggttctttt   1200

tttttatact ccaagctgac agtggacaag tctcgttggc aagaaggcaa cgtgttctct   1260

tgtagcgtga tgcacgaggc tttacacaac cactacaccc agaagtcttt atctctgtct   1320

ttaggc                                                              1326
```

```
<210> SEQ ID NO 37
<211> LENGTH: 642
<212> TYPE: DNA
<213> ORGANISM: Artificial Sequence
<220> FEATURE:
<223> OTHER INFORMATION: Nucleic acid molecule

<400> SEQUENCE: 37

gagatcgtga tgacccagtc cccagccaca ctgagcctgt ctgtgggaga gagggtgacc     60

ctgtcttgca aggcttccga gaacgtgggc ggctacgtga gctggtatca gcagaagccc    120

gaccagtctc ctaagctgct gatctacgga gcctccagca ggcacacagg agtgccagac    180

cggttcaccg gatccggaag cgagacagac ttcaccctga caatctcttc cgtgcaggct    240

gaggatctgg ccgcttatca ttgtggccag aattacatct atcccttcac ctttggcggc    300

ggcacaaagc tggagatcaa gcggaccgtg gctgcccct  ccgtgttcat cttcccccct    360

tccgacgagc agctgaagtc cggcaccgct agcgtggtgt gtttactgaa caacttctac    420

cctcgtgagg ccaaggtgca gtggaaggtg gacaacgctt tacagtccgg caactcccaa    480

gaatccgtga ccgagcaaga ttccaaggac tccacctact ctttatcctc cactttaact    540

ttatccaagg ccgactacga gaagcacaag gtgtacgctt gtgaggtgac ccatcaaggt    600

ttatcctccc ccgtgaccaa gtccttcaat cgtggcgagt gc                       642
```

```
<210> SEQ ID NO 38
<211> LENGTH: 642
<212> TYPE: DNA
<213> ORGANISM: Artificial Sequence
<220> FEATURE:
<223> OTHER INFORMATION: Nucleic acid molecule

<400> SEQUENCE: 38

gagatcgtga tgacccagtc cccagccaca ctgagcctgt ctgtgggaga gagggtgacc     60

ctgtcttgca aggcttccga gaacgtgggc ggctacgtga gctggtatca gcagaagccc    120

gaccagtctc ctaagctgct gatctacgga gcctccagca gggctacagg agtgccagac    180

cggttcaccg gatccggaag cgagacagac ttcaccctga caatctcttc cgtgcaggcc    240

gaggatctgg ccgcttatca ctgtggccag aattacatct atcccttcac ctttggcggc    300

ggcacaaagc tggagatcaa gcggaccgtg gctgcccct  ccgtgttcat cttcccccct    360

tccgacgagc agctgaagtc cggcaccgct agcgtggtgt gtttactgaa caacttctac    420

cctcgtgagg ccaaggtgca gtggaaggtg gacaacgctt tacagtccgg caactcccaa    480

gaatccgtga ccgagcaaga ttccaaggac tccacctact ctttatcctc cactttaact    540
```

```
ttatccaagg ccgactacga gaagcacaag gtgtacgctt gtgaggtgac ccatcaaggt    600

ttatcctccc ccgtgaccaa gtccttcaat cgtggcgagt gc                       642


<210> SEQ ID NO 39
<211> LENGTH: 642
<212> TYPE: DNA
<213> ORGANISM: Artificial Sequence
<220> FEATURE:
<223> OTHER INFORMATION: Nucleic acid molecule

<400> SEQUENCE: 39

gagatcgtga tgacccagag ccctgccaca ctgagcctgt ctgtgggcga gagggtgacc     60

ctgtcctgca aggcctccga gaacgtgggc ggctacgtgt cttggtatca gcagaagccc    120

gaccagtccc ctaagctgct gatctacgga gcctccagca ggcacaccgg agtgccagct    180

cggttctccg gaagcggatc tggcacagac tttaccctga caatctcttc cctggagcca    240

gaggatttcg ccgtgtatca ttgtggccag aattacatct atcccttcac ctttggcggc    300

ggcacaaagc tggagatcaa gcggaccgtg gctgcccccct ccgtgttcat cttcccccct    360

tccgacgagc agctgaagtc cggcaccgct agcgtggtgt gtttactgaa caacttctac    420

cctcgtgagg ccaaggtgca gtggaaggtg gacaacgctt tacagtccgg caactcccaa    480

gaatccgtga ccgagcaaga ttccaaggac tccacctact ctttatcctc cactttaact    540

ttatccaagg ccgactacga gaagcacaag gtgtacgctt gtgaggtgac ccatcaaggt    600

ttatcctccc ccgtgaccaa gtccttcaat cgtggcgagt gc                       642


<210> SEQ ID NO 40
<211> LENGTH: 642
<212> TYPE: DNA
<213> ORGANISM: Artificial Sequence
<220> FEATURE:
<223> OTHER INFORMATION: Nucleic acid molecule

<400> SEQUENCE: 40

gaaattgtgc tgactcagtc tcctgctact ctgtccctgt ctcctggtga acgggccact     60

ctgagctgca aggccagtga aaatgtgggt ggctatgtta gctggtatca gcaaaagccc    120

gaccagtctc ccaaactgct gatctacggc gcttccagtc ggcacacagg cgtgccagat    180

cgctttactg ggagcggctc tgagactgac ttcacactga ccattagcag tgtccaggcc    240

gaagatctcg cagcctatca ttgcggccag aactacatct atccattcac cttcggtgga    300

ggaaccaaac tggaaatcaa gcggaccgtg gctgcccccct ccgtgttcat cttcccccct    360

tccgacgagc agctgaagtc cggcaccgct agcgtggtgt gtttactgaa caacttctac    420

cctcgtgagg ccaaggtgca gtggaaggtg gacaacgctt tacagtccgg caactcccaa    480

gaatccgtga ccgagcaaga ttccaaggac tccacctact ctttatcctc cactttaact    540

ttatccaagg ccgactacga gaagcacaag gtgtacgctt gtgaggtgac ccatcaaggt    600

ttatcctccc ccgtgaccaa gtccttcaat cgtggcgagt gc                       642


<210> SEQ ID NO 41
<211> LENGTH: 10
<212> TYPE: PRT
<213> ORGANISM: Artificial Sequence
<220> FEATURE:
<223> OTHER INFORMATION: Heavy chainCDR1

<400> SEQUENCE: 41

Gly Tyr Ala Phe Thr Asn Tyr Trp Leu Gly
```

1 5 10

<210> SEQ ID NO 42
<211> LENGTH: 10
<212> TYPE: PRT
<213> ORGANISM: Artificial Sequence
<220> FEATURE:
<223> OTHER INFORMATION: Heavy chainCDR2

<400> SEQUENCE: 42

Asp Phe Tyr Pro Arg Thr Gly Asn Thr Phe
1 5 10

<210> SEQ ID NO 43
<211> LENGTH: 10
<212> TYPE: PRT
<213> ORGANISM: Artificial Sequence
<220> FEATURE:
<223> OTHER INFORMATION: Heavy chainCDR2

<400> SEQUENCE: 43

Gly Phe Tyr Pro Arg Thr Gly Asn Thr Phe
1 5 10

<210> SEQ ID NO 44
<211> LENGTH: 9
<212> TYPE: PRT
<213> ORGANISM: Artificial Sequence
<220> FEATURE:
<223> OTHER INFORMATION: Heavy chainCDR3

<400> SEQUENCE: 44

Ala Arg Ala Gly Thr Gly Phe Asp Tyr
1 5

<210> SEQ ID NO 45
<211> LENGTH: 8
<212> TYPE: PRT
<213> ORGANISM: Artificial Sequence
<220> FEATURE:
<223> OTHER INFORMATION: Light chainCDR1

<400> SEQUENCE: 45

Glu Asn Val Gly Gly Tyr Val Ser
1 5

<210> SEQ ID NO 46
<211> LENGTH: 7
<212> TYPE: PRT
<213> ORGANISM: Artificial Sequence
<220> FEATURE:
<223> OTHER INFORMATION: Light chainCDR2

<400> SEQUENCE: 46

Gly Ala Ser Ser Arg His Thr
1 5

<210> SEQ ID NO 47
<211> LENGTH: 7
<212> TYPE: PRT
<213> ORGANISM: Artificial Sequence
<220> FEATURE:
<223> OTHER INFORMATION: Light chainCDR2

<400> SEQUENCE: 47

Gly Ala Ser Ser Arg Ala Thr
1 5

```
<210> SEQ ID NO 48
<211> LENGTH: 7
<212> TYPE: PRT
<213> ORGANISM: Artificial Sequence
<220> FEATURE:
<223> OTHER INFORMATION: Light chainCDR3

<400> SEQUENCE: 48

Asn Tyr Ile Tyr Pro Phe Thr
1               5


<210> SEQ ID NO 49
<211> LENGTH: 330
<212> TYPE: PRT
<213> ORGANISM: Artificial Sequence
<220> FEATURE:
<223> OTHER INFORMATION: Full-length sequence of antibody constant
      region

<400> SEQUENCE: 49

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285
```

-continued

```
Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

HUMANIZED ANTI-TRKA ANTIBODIES AND USES THEREOF

CROSS-REFERENCE TO RELATED APPLICATION

This application claims the priority and benefits of Chinese Patent Application No. 202011307482.7, filed with the State Intellectual Property Office of China on Nov. 20, 2020, which is incorporated herein by reference in its entirety.

FIELD OF THE INVENTION

The present invention relates to the field of biotechnology. Specifically, the present invention relates to humanized anti-TrkA antibodies and uses thereof. More specifically, the present invention relates to a humanized antibody or antigen-binding fragment thereof, nucleic acid molecule, expression vector, recombinant cell, pharmaceutical composition, pharmaceutical use and a kit for detecting TrkA that can specifically recognize TrkA.

BACKGROUND ART

At present, non-opioid analgesics are mainly used clinically for mild to moderate pain, such as non-steroidal anti-inflammatory drugs (NSAIDs); opioid analgesics are mainly used for moderate to severe pain. However, NSAIDs have a "ceiling effect", and opioids only can effectively relieve less than 30% of non-tumor chronic pain, and 20% of patients with cancer pain have opioid resistance. In addition, NSAIDs have hidden dangers of gastrointestinal and cardiovascular safety, especially during long-term medication. For opioid analgesics, years of drug improvement experiments have failed to effectively reduce its addiction and many other side effects, and patients expect new safer and more effective drugs.

Nerve growth factor (NGF) is involved in the pathophysiological process of pain. It mainly activates the NGF/TrKA signaling pathway by binding to high-affinity tyrosine-nase (TrkA) receptors, which affects the release of inflammatory mediators, the opening of ion channels and the promotion of the growth of nerve fibers, thereby participating in the occurrence, conduction and sensitization process of pain. Studies have shown that blocking NGF-TrkA signaling pathway can effectively reduce pain and hyperalgesia, and NGF-TrkA signaling pathway is an effective target for the development of new analgesics. However, NGF may have a variety of undesirable agonist properties. TrkA monoclonal antibodies selectively target and bind to TrkA receptors, which can not only block the activation of the TrkA signaling pathway by NGF, effectively inhibit the transmission of pain signals, but also avoid unpredictable side effects such as bone and joint necrosis caused by excessive neutralization of NGF by using anti-NGF antibodies. Therefore, TrkA-targeted analgesic drugs targeting NGF-TrkA may represent a better treatment option.

The therapeutic and diagnostic applications of animal-derived monoclonal antibodies in humans have basic contraindications, especially for treatment regimens that require repeated administration. Specifically, murine monoclonal antibodies have a relatively short half-life, and lack some basic functional properties of immunoglobulins when used in humans, such as complement-dependent cytotoxicity and antibody-dependent cell-mediated cytotoxicity. In addition, non-human monoclonal antibodies contain immunogenic amino acid sequences if injected into patients. Although so-called chimeric antibodies (variable murine regions linked to human constant regions) have produced some positive results, there are still immunogenicity problems.

SUMMARY

This application is based on the inventors' discovery of the following issues and facts:

The NGF-TrkA signaling pathway is an effective target for the development of new analgesics. If TrkA monoclonal antibodies selectively target and bind to TrkA receptors, it can not only block the activation of the TrkA signaling pathway by NGF, effectively inhibit the transmission of pain signals, but also avoid unpredictable side effects such as bone and joint necrosis caused by excessive neutralization of NGF by using anti-NGF antibodies. However, because the TrkA molecule is a receptor membrane protein, it is more difficult to screen for blocking anti-TrkA monoclonal antibodies. In addition, designing blocking TrkA receptor antibodies has safety risks due to antibody-mediated immune responses. Therefore, it is difficult to design and develop monoclonal antibodies against TrkA.

The inventors of the present application not only successfully screened a new type of anti-TrkA monoclonal antibody with long-acting analgesic effect, but more importantly, the inventors humanized the murine anti-TrKA monoclonal antibody that was screened out into a humanized monoclonal antibody. Specifically, the FR regions and constant regions of the murine anti-TrKA monoclonal antibodies screened by hybridoma technology were replaced with human ones, and the CDRs of the variable regions of the murine anti-TrKA monoclonal antibodies were retained, and a series of humanized monoclonal antibodies against TrkA were obtained. The inventors found that the humanized antibody candidates obtained in this application had basically the same in vivo and in vitro activities as the human-mouse chimeric anti-TrkA monoclonal antibody 23E12, and not only could specifically target and bind to TrkA receptors, block the binding of NGF and TrkA, effectively inhibit pain, but also had lower immunogenicity and better pharmacokinetic parameters than the human-mouse chimeric anti-TrkA monoclonal antibody.

Among them, the human-mouse chimeric anti-TrkA monoclonal antibody 23E12 had the heavy chain variable region VH0 with the amino acid sequence shown in SEQ ID NO:1 and the light chain variable region VL0 with the amino acid sequence shown in SEQ ID NO:9.

In the first aspect of the present invention, the present invention provides a humanized antibody or antigen-binding fragment thereof capable of specifically recognizing TrkA. According to an embodiment of the present invention, the antibody or antigen-binding fragment thereof comprises a heavy chain variable region with the VH-CDR1 shown in SEQ ID NO:41, the VH-CDR2 shown in SEQ ID NO:42 or SEQ ID NO:43, and the VH-CDR3 shown in SEQ ID NO: 44; and

- a light chain variable region with the VL-CDR1 shown in SEQ ID NO:45, the VL-CDR2 shown in SEQ ID NO:46 or SEQ ID NO:47, and the VL-CDR3 shown in SEQ ID NO:48.

```
                                   (SEQ ID NO: 41)
GYAFTNYWLG.
                                   (SEQ ID NO: 42)
DFYPRTGNTF.
```

-continued (SEQ ID NO: 43)
GFYPRTGNTF.

(SEQ ID NO: 44)
ARAGTGFDY.

(SEQ ID NO: 45)
ENVGGYVS.

(SEQ ID NO: 46)
GASSRHT.

(SEQ ID NO: 47)
GASSRAT.

(SEQ ID NO: 48)
NYTYPFT

According to an embodiment of the present invention, the antibody or antigen-binding fragment thereof comprises a heavy chain variable region with the VH-CDR1 shown in SEQ ID NO:41, the VH-CDR2 shown in SEQ ID NO:42 and the VH-CDR3 shown in SEQ ID NO: 44; and a light chain variable region with the VL-CDR1 shown in SEQ ID NO:45, the VL-CDR2 shown in SEQ ID NO:46 and the VL-CDR3 shown in SEQ ID NO:48.

According to an embodiment of the present invention, the antibody or antigen-binding fragment thereof comprises a heavy chain variable region with the VH-CDR1 shown in SEQ ID NO:41, the VH-CDR2 shown in SEQ ID NO:43 and the VH-CDR3 shown in SEQ ID NO: 44; and a light chain variable region with the VL-CDR1 shown in SEQ ID NO:45, the VL-CDR2 shown in SEQ ID NO:46 and the VL-CDR3 shown in SEQ ID NO:48.

According to an embodiment of the present invention, the antibody or antigen-binding fragment thereof comprises a heavy chain variable region with the VH-CDR1 shown in SEQ ID NO:41, the VH-CDR2 shown in SEQ ID NO:42 and the VH-CDR3 shown in SEQ ID NO: 44; and a light chain variable region with the VL-CDR1 shown in SEQ ID NO:45, the VL-CDR2 shown in SEQ ID NO:47 and the VL-CDR3 shown in SEQ ID NO:48.

According to an embodiment of the present invention, the antibody or antigen-binding fragment thereof comprises a heavy chain variable region with the VH-CDR1 shown in SEQ ID NO:41, the VH-CDR2 shown in SEQ ID NO:43, and the VH-CDR3 shown in SEQ ID NO: 44; and a light chain variable region with the VL-CDR1 shown in SEQ ID NO:45, the VL-CDR2 shown in SEQ ID NO:47 and the VL-CDR3 shown in SEQ ID NO:48.

According to an embodiment of the present invention, the antibody or antigen-binding fragment thereof comprises a heavy chain variable region with the amino acid sequence shown in any one of SEQ ID NO: 2-8, and a light chain variable region with the amino acid sequence shown in any one of SEQ ID NO: 10-13. In the present application, the variable region includes murine CDRs and human framework regions.

In this application, SEQ ID NO: 2-8 are called VH1-VH7 in turn. SEQ ID NO: 10-13 are called VL1-VL4 in turn.

VH0:

(SEQ ID NO: 1)
QVQLQQSGAELVRPGTSVKISCKASGYAFTNYWLGWMKQRPGHGLEWIG
DFYPRTGNTFYNENFKGKVTLTADKSSNTAYMQLSSLTSEDSAVYLCAR
AGTGFDYWGQGTTLTVSS.

-continued

VH1:

(SEQ ID NO: 2)
EVQLLESGGGLVQPGGSLKLSCKASGYAFTNYWLGWMKQRPGHGLEWIG
DFYPRTGNTFYNENFKGKVTLTADKSSNTAYMQLSSLTSEDSAVYLCAR
AGTGFDYWGQGTTLTVSS.

VH2:

(SEQ ID NO: 3)
EVQLLESGGGLVQPGGSLKLSCKASGYAFTNYWLGWMKQRPGHGLEWIG
GFYPRTGNTFYNENFKGKVTLTADKSSNTAYMQLSSLTSEDSAVYLCAR
AGTGFDYWGQGTTLTVSS.

VH3:

(SEQ ID NO: 4)
EVQLLESGGGLVQPGGSLKLSCKASGYAFTNYWLGWMKQRPGHGLEWIG
DFYPRTGNTFYNENFKGQVTMSVDKSITTAYLQWNSLKASDTAMYYCAR
AGTGFDYWGQGTTLTVSS.

VH4:

(SEQ ID NO: 5)
QVQLVQSGVEVKKPGASVKVSCKASGYAFTNYWLGWMKQRPGHGLEWIG
DFYPRTGNTFYNENFKGQVTMSVDKSITTAYLQWNSLKASDTAMYYCAR
AGTGFDYWGQGTTLTVSS.

VH5:

(SEQ ID NO: 6)
QVQLVQSGVEVKKPGASVKVSCKASGYAFTNYWLGWMKQRPGHGLEWIG
DFYPRTGNTFYNENFKGKVTITADKSITTAYMQLSSLKASDTAVYYCAR
AGTGFDYWGQGTTLTVSS.

VH6:

(SEQ ID NO: 7)
QVQLVQSGVEVKKPGASVKVSCKASGYAFTNYWLGWVKQRPGHGLEWIG
DFYPRTGNTFYNENFKGKVTITADKSITTAYMQLSSLKASDTAVYYCAR
AGTGFDYWGQGTTLTVSS.

VH7:

(SEQ ID NO: 8)
QVQLVQSGVEVKKPGASVKVSCKASGYAFTNYWLGWMKQRPGHGLEWIG
DFYPRTGNTFYNENFKGKVTLTADKSSNTAYMQLSSLTSEDSAVYLCAR
AGTGFDYWGQGTTLTVSS.

VL0:

(SEQ ID NO: 9)
SIVMTQSPKSMSMSVGERVTLSCKASENVGGYVSWYQQKPDQSPKLLIY
GASSRHTGVPDRFTGSGSETDFTLTISSVQAEDLAAYHCGQNYIYPFTF
GGGTKLEIK.

VL1:

(SEQ ID NO: 10)
EIVMTQSPATLSLSVGERVTLSCKASENVGGYVSWYQQKPDQSPKLLIY
GASSRHTGVPDRFTGSGSETDFTLTISSVQAEDLAAYHCGQNYIYPFTF
GGGTKLEIK.

VL2:

(SEQ ID NO: 11)
EIVMTQSPATLSLSVGERVTLSCKASENVGGYVSWYQQKPDQSPKLLIY
GASSRATGVPDRFTGSGSETDFTLTISSVQAEDLAAYHCGQNYIYPFTF
GGGTKLEIK.

VL3:

(SEQ IDNO: 12)
EIVMTQSPATLSLSVGERVTLSCKASENVGGYVSWYQQKPDQSPKLLIY
GASSRHTGVPARFSGSGSGTDFTLTISSLEPEDFAVYHCGQNYIYPFTF
GGGTKLEIK.

VL4:

(SEQ ID NO: 13)
EIVLTQSPATLSLSPGERATLSCKASENVGGYVSWYQQKPDQSPKLLIY
GASSRHTGVPDRFTGSGSETDFTLTISSVQAEDLAAYHCGQNYIYPFTF
GGGTKLEIK.

Among them, the underlined parts are the CDR sequence of the heavy chain variable region and the CDR sequence of the light chain variable region, respectively.

According to an embodiment of the present invention, the antibody or antigen-binding fragment thereof comprises a heavy chain variable region and a light chain variable region selected from:

(a) the heavy chain variable region with the amino acid sequence shown in SEQ ID NO: 2 and the light chain variable region with the amino acid sequence shown in SEQ ID NO: 10;

(b) the heavy chain variable region with the amino acid sequence shown in SEQ ID NO: 4 and the light chain variable region with the amino acid sequence shown in SEQ ID NO: 10; or (c) the heavy chain variable region with the amino acid sequence shown in SEQ ID NO: 4 and the light chain variable region with the amino acid sequence shown in SEQ ID NO: 11.

According to an embodiment of the present invention, the antibody or antigen-binding fragment thereof specifically recognizes the extracellular region of TrkA.

According to an embodiment of the present invention, the antibody comprises at least one of a heavy chain framework region sequence and a light chain framework region sequence, and both the heavy chain framework region sequence and the light chain framework region sequence are derived from human IgG antibodies or their mutants. Furthermore, the immunogenicity of the antibody can be effectively reduced.

According to an embodiment of the present invention, the light chain constant region of the antibody is derived from a human Kappa light chain constant region; the heavy chain constant region is derived from a human IgG4 heavy chain constant region.

According to an embodiment of the present invention, the Fc region of the antibody has S10P, F16A, L17A, R191K mutations and 229 K deletion mutations compared with human IgG4 wild-type Fc. Wherein, the location of the above-mentioned amino acid position is based on the amino acid sequence shown in SEQ ID NO: 16 of the human IgG4 wild-type Fc sequence. For example, S10P means that the 10th S of the amino acid sequence shown in SEQ ID NO: 16 is mutated to P, and so on. The inventors found that after the Fc region of the antibody had the above mutations and deletions, the safety and stability of the antibody could be significantly improved, and the half-life of the antibody in the body was also significantly prolonged.

```
                                        (SEQ ID NO: 16)
ESKYGPPCPSCPAPEFLGGPSVFLFPPKPKDTLMISRTPEVTCVVVDVS

QEDPEVQFNWYVDGVEVHNAKTKPREEQFNSTYRVVSVLTVLHQDWLNG

KEYKCKVSNKGLPSSIEKTISKAKGQPREPQVYTLPPSQEEMTKNQVSL

TCLVKGFYPSDIAVEWESNGQPENNYKTTPPVLDSDGSFFLYSRLTVDK

SRWQEGNVFSCSVMHEALHNHYTQKSLSLSLGK.
```

According to an embodiment of the present invention, the full-length sequence of the constant region of the antibody is as shown in SEQ ID NO: 14 or 15.

```
                                        (SEQ ID NO: 14)
RTVAAPSVFIFPPSDEQLKSGTASVVCLLNNFYPREAKVQWKVDNALQS
GNSQESVTEQDSKDSTYSLSSTLTLSKADYEKHKVYACEVTHQGLSSPV
TKSFNRGEC.

                                        (SEQ ID NO: 15)
ASTKGPSVFPLAPCSRSTSESTAALGCLVKDYFPEPVTVSWNSGALTSG

VHTFPAVLQSSGLYSLSSVVTVPSSSLGTKTYTCNVDHKPSNTKVDKRV

ESKYGPPCPPCPAPEAAGGPSVFLFPPKPKDTLMISRTPEVTCVVVDVS
```

-continued

```
QEDPEVQFNWYVDGVEVHNAKTKPREEQFNSTYRVVSVLTVLHQDWLNG

KEYKCKVSNKGLPSSIEKTISKAKGQPREPQVYTLPPSQEEMTKNQVSL

TCLVKGFYPSDIAVEWESNGQPENNYKTTPPVLDSDGSFFLYSKLTVDK

SRWQEGNVFSCSVMHEALHNHYTQKSLSLSLG.
```

Wherein, the full-length sequence of the constant region of the antibody shown in SEQ ID NO: 14 is an IgG4 light chain constant region. The full-length sequence of the constant region of the antibody shown in SEQ ID NO: 15 includes the IgG4 heavy chain constant region and the Fc region, wherein the IgG4 heavy chain constant region sequence is ASTKGPSVFPLAPCSRSTSESTAAL-GCLVKDYFPEPVTVSWNSGALTSGVHTFPAVLQSSG LYS-LSSVVTVPSSSLGTKTYTCNVDHKPSNTKVDKRV, the sequence of the Fc region is

```
ESKYGPPCPPCPAPEAAGGPSVFLFPPKPKDTLMISRTPEVTCVVVDVS

QEDPEVQFNWYVDGVEVHNAKTKPREEQFNSTYRVVSVLTVLHQDWLNG

KEYKCKVSNKGLPSSIEKTISKAKGQPREPQVYTLPPSQEEMTKNQVSL

TCLVKGFYPSDIAVEWESNGQPENNYKTTPPVLDSDGSFFLYSKLTVDK

SRWQEGNVFSCSVMHEALHNHYTQKSLSLSLG.
```

According to an embodiment of the present invention, the antibody comprises a heavy chain with the amino acid sequence shown in any one of SEQ ID NO: 17-23 and a light chain with the amino acid sequence shown in any one of SEQ ID NO: 24-27. In this application, SEQ ID NO: 17-23 are called H1-H7 in turn. SEQ ID NO: 24-27 are called L1-L4 in turn. In addition, the human-mouse chimeric anti-TrkA monoclonal antibody 23E12 has a heavy chain H0 with the amino acid sequence shown in SEQ ID NO: 28 and a light chain L0 with the amino acid sequence shown in SEQ ID NO: 29.

```
H1:
                                        (SEQ ID NO: 17)
EVQLLESGGGLVQPGGSLKLSCKASGYAFTNYWLGWMKQRPGHGLEWIG

DFYPRTGNTFYNENFKGKVTLTADKSSNTAYMQLSSLTSEDSAVYLCAR

AGTGFDYWGQGTTLTVSSASTKGPSVFPLAPCSRSTSESTAALGCLVKD

YFPEPVTVSWNSGALTSGVHTFPAVLQSSGLYSLSSVVTVPSSSLGTKT

YTCNVDHKPSNTKVDKRVESKYGPPCPPCPAPEAAGGPSVFLFPPKPKD

TLMISRTPEVTCVVVDVSQEDPEVQFNWYVDGVEVHNAKTKPREEQFNS

TYRVVSVLTVLHQDWLNGKEYKCKVSNKGLPSSIEKTISKAKGQPREPQ

VYTLPPSQEEMTKNQVSLTCLVKGFYPSDIAVEWESNGQPENNYKTTPP

VLDSDGSFFLYSKLTVDKSRWQEGNVFSCSVMHEALHNHYTQKSLSLSL

G.

H2:
                                        (SEQ ID NO: 18)
EVQLLESGGGLVQPGGSLKLSCKASGYAFTNYWLGWMKQRPGHGLEWIG

GFYPRTGNTFYNENFKGKVTLTADKSSNTAYMQLSSLTSEDSAVYLCAR

AGTGFDYWGQGTTLTVSSASTKGPSVFPLAPCSRSTSESTAALGCLVKD
```

-continued

YFPEPVTVSWNSGALTSGVHTFPAVLQSSGLYSLSSVVTVPSSSLGTKT

YTCNVDHKPSNTKVDKRVESKYGPPCPPCPAPEAAGGPSVFLFPPKPKD

TLMISRTPEVTCVVVDVSQEDPEVQFNWYVDGVEVHNAKTKPREEQFNS

TYRVVSVLTVLHQDWLNGKEYKCKVSNKGLPSSIEKTISKAKGQPREPQ

VYTLPPSQEEMTKNQVSLTCLVKGFYPSDIAVEWESNGQPENNYKTTPP

VLDSDGSFFLYSKLTVDKSRWQEGNVFSCSVMHEALHNHYTQKSLSLSL

G.

H3:

(SEQ ID NO: 19)

EVQLLESGGGLVQPGGSLKLSCKASGYAFTNYWLGWMKQRPGHGLEWIG

DFYPRTGNTFYNENFKGQVTMSVDKSITTAYLQWNSLKASDTAMYYCAR

AGTGFDYWGQGTTLTVSSASTKGPSVFPLAPCSRSTSESTAALGCLVKD

YFPEPVTVSWNSGALTSGVHTFPAVLQSSGLYSLSSVVTVPSSSLGTKT

YTCNVDHKPSNTKVDKRVESKYGPPCPPCPAPEAAGGPSVFLFPPKPKD

TLMISRTPEVTCVVVDVSQEDPEVQFNWYVDGVEVHNAKTKPREEQFNS

TYRVVSVLTVLHQDWLNGKEYKCKVSNKGLPSSIEKTISKAKGQPREPQ

VYTLPPSQEEMTKNQVSLTCLVKGFYPSDIAVEWESNGQPENNYKTTPP

VLDSDGSFFLYSKLTVDKSRWQEGNVFSCSVMHEALHNHYTQKSLSLSL

G.

H4:

(SEQ ID NO: 20)

QVQLVQSGVEVKKPGASVKVSCKASGYAFTNYWLGWMKQRPGHGLEWIG

DFYPRTGNTFYNENFKGQVTMSVDKSITTAYLQWNSLKASDTAMYYCAR

AGTGFDYWGQGTTLTVSSASTKGPSVFPLAPCSRSTSESTAALGCLVKD

YFPEPVTVSWNSGALTSGVHTFPAVLQSSGLYSLSSVVTVPSSSLGTKT

YTCNVDHKPSNTKVDKRVESKYGPPCPPCPAPEAAGGPSVFLFPPKPKD

TLMISRTPEVTCVVVDVSQEDPEVQFNWYVDGVEVHNAKTKPREEQFNS

TYRVVSVLTVLHQDWLNGKEYKCKVSNKGLPSSIEKTISKAKGQPREPQ

VYTLPPSQEEMTKNQVSLTCLVKGFYPSDIAVEWESNGQPENNYKTTPP

VLDSDGSFFLYSKLTVDKSRWQEGNVFSCSVMHEALHNHYTQKSLSLSL

G.

H5:

(SEQ ID NO: 21)

QVQLVQSGVEVKKPGASVKVSCKASGYAFTNYWLGWMKQRPGHGLEWIG

DFYPRTGNTFYNENFKGKVTITADKSITTAYMQLSSLKASDTAVYYCAR

AGTGFDYWGQGTTLTVSSASTKGPSVFPLAPCSRSTSESTAALGCLVKD

YFPEPVTVSWNSGALTSGVHTFPAVLQSSGLYSLSSVVTVPSSSLGTKT

YTCNVDHKPSNTKVDKRVESKYGPPCPPCPAPEAAGGPSVFLFPPKPKD

TLMISRTPEVTCVVVDVSQEDPEVQFNWYVDGVEVHNAKTKPREEQFNS

TYRVVSVLTVLHQDWLNGKEYKCKVSNKGLPSSIEKTISKAKGQPREPQ

VYTLPPSQEEMTKNQVSLTCLVKGFYPSDIAVEWESNGQPENNYKTTPP

VLDSDGSFFLYSKLTVDKSRWQEGNVFSCSVMHEALHNHYTQKSLSLSL

G.

-continued

H6:

(SEQ ID NO: 22)

QVQLVQSGVEVKKPGASVKVSCKASGYAFTNYWLGWVKQRPGHGLEWIG

DFYPRTGNTFYNENFKGKVTITADKSITTAYMQLSSLKASDTAVYYCAR

AGTGFDYWGQGTTLTVSSASTKGPSVFPLAPCSRSTSESTAALGCLVKD

YFPEPVTVSWNSGALTSGVHTFPAVLQSSGLYSLSSVVTVPSSSLGTKT

YTCNVDHKPSNTKVDKRVESKYGPPCPPCPAPEAAGGPSVFLFPPKPKD

TLMISRTPEVTCVVVDVSQEDPEVQFNWYVDGVEVHNAKTKPREEQFNS

TYRVVSVLTVLHQDWLNGKEYKCKVSNKGLPSSIEKTISKAKGQPREPQ

VYTLPPSQEEMTKNQVSLTCLVKGFYPSDIAVEWESNGQPENNYKTTPP

VLDSDGSFFLYSKLTVDKSRWQEGNVFSCSVMHEALHNHYTQKSLSLSL

G.

H7:

(SEQ ID NO: 23)

QVQLVQSGVEVKKPGASVKVSCKASGYAFTNYWLGWMKQRPGHGLEWIG

DFYPRTGNTFYNENFKGKVTLTADKSSNTAYMQLSSLTSEDSAVYLCAR

AGTGFDYWGQGTTLTVSSASTKGPSVFPLAPCSRSTSESTAALGCLVKD

YFPEPVTVSWNSGALTSGVHTFPAVLQSSGLYSLSSVVTVPSSSLGTKT

YTCNVDHKPSNTKVDKRVESKYGPPCPPCPAPEAAGGPSVFLFPPKPKD

TLMISRTPEVTCVVVDVSQEDPEVQFNWYVDGVEVHNAKTKPREEQFNS

TYRVVSVLTVLHQDWLNGKEYKCKVSNKGLPSSIEKTISKAKGQPREPQ

VYTLPPSQEEMTKNQVSLTCLVKGFYPSDIAVEWESNGQPENNYKTTPP

VLDSDGSFFLYSKLTVDKSRWQEGNVFSCSVMHEALHNHYTQKSLSLSL

G.

L1:

(SEQ ID NO: 24)

EIVMTQSPATLSLSVGERVTLSCKASENVGGYVSWYQQKPDQSPKLLIY

GASSRHTGVPDRFTGSGSETDFTLTISSVQAEDLAAYHCGQNYIYPFTF

GGGTKLEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC.

L2:

(SEQ ID NO: 25)

EIVMTQSPATLSLSVGERVTLSCKASENVGGYVSWYQQKPDQSPKLLIY

GASSRATGVPDRFTGSGSETDFTLTISSVQAEDLAAYHCGQNYIYPFTF

GGGTKLEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC.

L3:

(SEQ ID NO: 26)

EIVMTQSPATLSLSVGERVTLSCKASENVGGYVSWYQQKPDQSPKLLIY

GASSRHTGVPARFSGSGSGTDFTLTISSLEPEDFAVYHCGQNYIYPFTF

GGGTKLEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC.

-continued

L4:

(SEQ ID NO: 27)
EIVLTQSPATLSLSPGERATLSCKASENVGGYVSWYQQKPDQSPKLLIY
GASSRHTGVPDRFTGSGSETDFTLTISSVQAEDLAAYHCGQNYIYPFTF
GGGTKLEIKRTVAAPSVFIFPPSDEQLKSGTASVVCLLNNFYPREAKVQ
WKVDNALQSGNSQESVTEQDSKDSTYSLSSTLTLSKADYEKHKVYACEV
THQGLSSPVTKSFNRGEC.

H0:

(SEQ ID NO: 28)
QVQLQQSGAELVRPGTSVKISCKASGYAFTNYWLGWMKQRPGHGLEWIG
DFYPRTGNTFYNENFKGKVTLTADKSSNTAYMQLSSLTSEDSAVYLCAR
AGTGFDYWGQGTTLTVSSASTKGPSVFPLAPCSRSTSESTAALGCLVKD
YFPEPVTVSWNSGALTSGVHTFPAVLQSSGLYSLSSVVTVPSSSLGTKT
YTCNVDHKPSNTKVDKRVESKYGPPCPPCPAPEAAGGPSVFLFPPKPKD
TLMISRTPEVTCVVVDVSQEDPEVQFNWYVDGVEVHNAKTKPREEQFNS
TYRVVSVLTVLHQDWLNGKEYKCKVSNKGLPSSIEKTISKAKGQPREPQ
VYTLPPSQEEMTKNQVSLTCLVKGFYPSDIAVEWESNGQPENNYKTTPP
VLDSDGSFFLYSKLTVDKSRWQEGNVFSCSVMHEALHNHYTQKSLSLSL
G.

L0:

(SEQ ID NO: 29)
SIVMTQSPKSMSMSVGERVTLSCKASENVGGYVSWYQQKPDQSPKLLIY
GASSRHTGVPDRFTGSGSETDFTLTISSVQAEDLAAYHCGQNYIYPFTF
GGGTKLEIKRTVAAPSVFIFPPSDEQLKSGTASVVCLLNNFYPREAKVQ
WKVDNALQSGNSQESVTEQDSKDSTYSLSSTLTLSKADYEKHKVYACEV
THQGLSSPVTKSFNRGEC.

(SEQ ID NO: 49)
ASTKGPSVFPLAPSSKSTSGGTAALGCLVKDYFPEPVTVSWNSGALTSG
VHTFPAVLQSSGLYSLSSVVTVPSSSLGTQTYICNVNHKPSNTKVDKKV
EPKSCDKTHTCPPCPAPELLGGPSVFLFPPKPKDTLMISRTPEVTCVVV
DVSHEDPEVKFNWYVDGVEVHNAKTKPREEQYNSTYRVVSVLTVLHQDW
LNGKEYKCKVSNKALPAPIEKTISKAKGQPREPQVYTLPPSREEMTKNQ
VSLTCLVKGFYPSDIAVEWESNGQPENNYKTTPPVLDSDGSFFLYSKLT
VDKSRWQQGNVFSCSVMHEALHNHYTQKSLSLSPGK.

The full-length sequence of the constant region of the antibody shown in SEQ ID NO: 49 includes the IgG1 heavy chain constant region and the Fc region, wherein the IgG1 heavy chain is constant region sequence ASTKGPSVFPLAPSSKSTSGGTAALGCLVKDYFPEPVTVSWNSGALTSG
VHTFPAVLQSSGLYSLSSVVTVPSSSLGTQTYICNVNHKPSNTKVDKKV
and the Fc region sequence is
EPKSCDKTHTCPPCPAPELLGGPSVFLFPPKPKDTLMISRTPEVTCVVV
DVSHEDPEVKFNWYVDGVEVHNAKTKPREEQYNSTYRVVSVLTVLHQDW
LNGKEYKCKVSNKALPAPIEKTISKAKGQPREPQVYTLPPSREEMTKNQ -continued VSLTCLVKGFYPSDIAVEWESNGQPENNYKTTPPVLDSDGSFFLYSKLT
VDKSRWQQGNVFSCSVMHEALHNHYTQKSLSLSPGK.

According to an embodiment of the present invention, the antibody comprises a heavy chain and a light chain selected from the group selected from:

(a) the heavy chain with the amino acid sequence shown in SEQ ID NO: 17 and the light chain with the amino acid sequence shown in SEQ ID NO: 24;

(b) the heavy chain with the amino acid sequence shown in SEQ ID NO: 19 and the light chain with the amino acid sequence shown in SEQ ID NO: 24; or (c) the heavy chain with the amino acid sequence shown in SEQ ID NO: 19 and the light chain with the amino acid sequence shown in SEQ ID NO: 25.

In this application, the humanized monoclonal antibody composed of the above-mentioned H1 and L1 with the IGHG4 heavy chain isotype and the Kappa isotype light chain is called H1L1-IgG4, the antibody composed of the above H3 and L1 with the IGHG4 heavy chain isotype and the Kappa isotype light chain is called H3L1-IgG4, and the antibody composed of the above H3 and L2 with the IGHG4 heavy chain isotype and the Kappa isotype light chain is called H3L2-IgG4, the humanized monoclonal antibody composed of the above-mentioned H1 and L1 with the IGHG1 heavy chain isotype and the Kappa isotype light chain is called H1L1-IgG1, and so on.

According to an embodiment of the present invention, the antibody is a single-chain antibody, a multimeric antibody, or a CDR-grafted antibody.

According to an embodiment of the present invention, the single-chain antibody comprises a heavy chain variable region with the amino acid sequence shown in any one of SEQ ID NO: 2-8 and a light chain variable region with the amino acid sequence shown in any one of SEQ ID NO: 10-13, wherein the C-terminus of the heavy chain variable region is connected to the N-terminus of the light chain variable region through a connecting peptide linker, or the C-terminus of the light chain variable region is connected to the N-terminus of the heavy chain variable region through a connecting peptide linker. It should be noted that the "connecting peptide linker" of the single-chain antibody described in this application is a connecting peptide used to connect the heavy chain variable region and the light chain variable region of the antibody. It can be a commonly used connecting peptide linker for the preparation of single-chain antibodies, or it can be a connecting peptide linker modified by scientific researchers. In some embodiments, the connecting peptide may be a G-rich polypeptide, for example, it may be selected from (G) 3-S (i.e., "GGGS"), (G)4-S (i.e., "GGGGS") and (G)5-S (i.e., "GGGGGS"), such as GGGGSGGGGSGGGGS.

According to an embodiment of the present invention, the antigen-binding fragment comprises at least one of Fab, Fab', F(ab)2, F(ab')2, Fv, scFv-Fc fusion protein, scFv-Fv fusion protein, and minimum recognition unit.

In the second aspect of the present invention, the present invention provides a nucleic acid molecule. According to an embodiment of the present invention, the nucleic acid molecule encodes the aforementioned antibody or antigen-binding fragment thereof. The antibody or antigen-binding fragment encoded by the nucleic acid molecule according to the embodiment of the present invention can specifically target and bind to TrkA and block the binding of NGF and TrkA.

According to an embodiment of the present invention, the aforementioned nucleic acid molecule may further include at least one of the following additional technical features:

According to an embodiment of the present invention, the nucleic acid molecule is DNA.

According to an embodiment of the present invention, the nucleic acid molecule comprises the nucleotide sequence shown in any one of SEQ ID NO: 30-36 or comprises the nucleotide sequence shown in any one of SEQ ID NO: 37-40.

(SEQ ID NO: 30)

GAGGTGCAGCTGCTGGAGTCTGGAGGAGGACTGGTGCAGCCAGGAGGCTCTCT
GAAGCTGTCCTGCAAGGCCAGCGGCTACGCTTTCACCAACTATTGGCTGGGATGGAT
GAAGCAGAGGCCAGGACACGGACTGGAGTGGATCGGCGACTTTTACCCTCGGACCG
GCAACACATTCTATAACGAGAACTTCAAGGGCAAGGTGACCCTGACAGCCGATAAGT
CCAGCAATACCGCTTACATGCAGCTGTCTTCCCTGACATCCGAGGACTCCGCCGTGTA
CCTGTGCGCTAGGGCTGGAACCGGATTCGATTATTGGGGCCAGGGCACCACACTGAC
AGTGAGCTCTGCCAGCACCAAGGGCCCCAGCGTGTTCCCTCTGGCTCCTTGTAGCCG
GTCCACCTCCGAGTCCACAGCTGCTCTGGGCTGCCTCGTGAAGGACTACTTTCCCGA
ACCCGTTACCGTGAGCTGGAATAGCGGCGCTTTAACCTCCGGAGTGCACACCTTCCC
CGCTGTGCTCCAGTCCTCCGGTTTATACTCTTTATCCTCCGTGGTGACCGTGCCTTCCT
CCAGCCTCGGCACCAAGACCTACACTTGTAACGTGGACCACAAGCCCAGCAACACC
AAGGTGGACAAGAGGGTGGAGTCCAAGTACGGACCTCCTTGTCCCCCTTGCCCCGCC
CCCGAGGCCGCTGGCGGACCCTCCGTGTTCCTCTTCCCCCCCAAACCCAAGGACACT
TTAATGATCTCCCGGACCCCCGAAGTGACTTGTGTGGTGGTGGACGTGTCCCAAGAA
GACCCCGAGGTGCAGTTTAACTGGTACGTGGATGGCGTGGAGGTGCACAACGCCAA
GACCAAGCCTAGGGAGGAACAGTTCAACTCCACCTACCGGGTGGTGTCCGTGCTCAC
CGTGCTGCATCAAGATTGGCTGAACGGCAAGGAGTACAAGTGCAAGGTGAGCAACA
AGGGACTGCCCAGCTCCATCGAGAAGACCATCAGCAAGGCCAAAGGCCAGCCCCGG
GAACCTCAAGTTTATACACTGCCCCCCAGCCAAGAAGAGATGACCAAGAACCAAGTT
TCTTTAACTTGTTTAGTGAAGGGCTTCTACCCTAGCGACATCGCTGTGGAGTGGGAGT
CCAATGGCCAGCCCGAAAACAATTATAAGACCACCCCCCCCGTGCTGGACTCCGATG
GTTCTTTTTTTTTATACTCCAAGCTGACAGTGGACAAGTCTCGTTGGCAAGAAGGCAA
CGTGTTCTCTTGTAGCGTGATGCACGAGGCTTTACACAACCACTACACCCAGAAGTCT
TTATCTCTGTCTTTAGGC.

(SEQ ID NO: 31)

GAGGTGCAGCTGCTGGAGAGCGGCGGCGGCCTGGTGCAGCCCGGCGGCAGCCT
GAAGCTGAGCTGCAAGGCCAGCGGCTACGCCTTCACCAACTACTGGCTGGGCTGGAT
GAAGCAGAGGCCCGGCCACGGCCTGGAGTGGATCGGCGGCTTCTACCCCAGGACCG
GCAACACCTTCTACAACGAGAACTTCAAGGGCAAGGTGACCCTGACCGCCGACAAG
AGCAGCAACACCGCCTACATGCAGCTGAGCAGCCTGACCAGCGAGGACAGCGCCGT
GTACCTGTGCGCCAGGGCCGGCACCGGCTTCGACTACTGGGGCCAGGGCACCACCCT
GACCGTGAGCAGCGCCAGCACCAAGGGCCCCAGCGTGTTCCCTCTGGCTCCTTGTAG
CCGGTCCACCTCCGAGTCCACAGCTGCTCTGGGCTGCCTCGTGAAGGACTACTTTCC
CGAACCCGTTACCGTGAGCTGGAATAGCGGCGCTTTAACCTCCGGAGTGCACACCTT
CCCCGCTGTGCTCCAGTCCTCCGGTTTATACTCTTTATCCTCCGTGGTGACCGTGCCTT
CCTCCAGCCTCGGCACCAAGACCTACACTTGTAACGTGGACCACAAGCCCAGCAACA
CCAAGGTGGACAAGAGGGTGGAGTCCAAGTACGGACCTCCTTGTCCCCCTTGCCCCG

-continued

CCCCCGAGGCCGCTGGCGGACCCTCCGTGTTCCTCTTCCCCCCCAAACCCAAGGACA

CTTTAATGATCTCCCGGACCCCCGAAGTGACTTGTGTGGTGGTGGACGTGTCCCAAG

AAGACCCCGAGGTGCAGTTTAACTGGTACGTGGATGGCGTGGAGGTGCACAACGCC

AAGACCAAGCCTAGGGAGGAACAGTTCAACTCCACCTACCGGGTGGTGTCCGTGCTC

ACCGTGCTGCATCAAGATTGGCTGAACGGCAAGGAGTACAAGTGCAAGGTGAGCAA

CAAGGGACTGCCCAGCTCCATCGAGAAGACCATCAGCAAGGCCAAAGGCCAGCCCC

GGGAACCTCAAGTTTATACACTGCCCCCCAGCCAAGAAGAGATGACCAAGAACCAA

GTTTCTTTAACTTGTTTAGTGAAGGGCTTCTACCCTAGCGACATCGCTGTGGAGTGGG

AGTCCAATGGCCAGCCCGAAAACAATTATAAGACCACCCCCCCCGTGCTGGACTCCG

ATGGTTCTTTTTTTTTATACTCCAAGCTGACAGTGGACAAGTCTCGTTGGCAAGAAGG

CAACGTGTTCTCTTGTAGCGTGATGCACGAGGCTTTACACAACCACTACACCCAGAA

GTCTTTATCTCTGTCTTTAGGC.

(SEQ ID NO: 32)

GAGGTGCAGCTGCTGGAGTCCGGAGGAGGACTGGTGCAGCCAGGAGGCTCTCT

GAAGCTGTCCTGCAAGGCCAGCGGCTACGCTTTCACCAACTATTGGCTGGGATGGAT

GAAGCAGAGGCCAGGACACGGACTGGAGTGGATCGGCGACTTTTACCCTCGGACCG

GCAATACATTCTATAACGAGAACTTCAAGGGCCAGGTGACAATGTCTGTGGATAAGTC

CATCACCACAGCCTACCTGCAGTGGAACAGCCTGAAGGCCTCTGACACCGCTATGTA

CTATTGTGCCAGGGCTGGCACAGGCTTCGATTATTGGGGCCAGGGCACCACACTGAC

CGTGTCCAGCGCCAGCACCAAGGGCCCCAGCGTGTTCCCTCTGGCTCCTTGTAGCCG

GTCCACCTCCGAGTCCACAGCTGCTCTGGGCTGCCTCGTGAAGGACTACTTTCCCGA

ACCCGTTACCGTGAGCTGGAATAGCGGCGCTTTAACCTCCGGAGTGCACACCTTCCC

CGCTGTGCTCCAGTCCTCCGGTTTATACTCTTTATCCTCCGTGGTGACCGTGCCTTCCT

CCAGCCTCGGCACCAAGACCTACACTTGTAACGTGGACCACAAGCCCAGCAACACC

AAGGTGGACAAGAGGGTGGAGTCCAAGTACGGACCTCCTTGTCCCCCTTGCCCCGCC

CCCGAGGCCGCTGGCGGACCCTCCGTGTTCCTCTTCCCCCCCAAACCCAAGGACACT

TTAATGATCTCCCGGACCCCCGAAGTGACTTGTGTGGTGGTGGACGTGTCCCAAGAA

GACCCCGAGGTGCAGTTTAACTGGTACGTGGATGGCGTGGAGGTGCACAACGCCAA

GACCAAGCCTAGGGAGGAACAGTTCAACTCCACCTACCGGGTGGTGTCCGTGCTCAC

CGTGCTGCATCAAGATTGGCTGAACGGCAAGGAGTACAAGTGCAAGGTGAGCAACA

AGGGACTGCCCAGCTCCATCGAGAAGACCATCAGCAAGGCCAAAGGCCAGCCCCGG

GAACCTCAAGTTTATACACTGCCCCCCAGCCAAGAAGAGATGACCAAGAACCAAGTT

TCTTTAACTTGTTTAGTGAAGGGCTTCTACCCTAGCGACATCGCTGTGGAGTGGGAGT

CCAATGGCCAGCCCGAAAACAATTATAAGACCACCCCCCCCGTGCTGGACTCCGATG

GTTCTTTTTTTTTATACTCCAAGCTGACAGTGGACAAGTCTCGTTGGCAAGAAGGCAA

CGTGTTCTCTTGTAGCGTGATGCACGAGGCTTTACACAACCACTACACCCAGAAGTCT

TTATCTCTGTCTTTAGGC.

(SEQ ID NO: 33)

CAAGTGCAACTGGTTCAATCTGGAGTGGAAGTTAAGAAGCCTGGTGCCAGCGTT

AAAGTGAGTTGCAAAGCCAGCGGATATGCCTTTACCAACTATTGGCTGGGCTGGATG

AAACAGAGGCCTGGCCATGGTCTGGAATGGATCGGAGACTTTTATCCACGCACCGGC

AACACATTCTATAACGAGAACTTCAAAGGTCAGGTGACCATGTCCGTGGATAAGAGC

-continued

ATCACTACCGCTTACCTCCAGTGGAACAGTCTGAAGGCTTCTGACACCGCCATGTACT

ACTGCGCTAGGGCAGGCACCGGGTTCGACTACTGGGGTCAAGGGACCACCCTCACC

GTGAGTAGCGCCAGCACCAAGGGCCCCAGCGTGTTCCCTCTGGCTCCTTGTAGCCGG

TCCACCTCCGAGTCCACAGCTGCTCTGGGCTGCCTCGTGAAGGACTACTTTCCCGAA

CCCGTTACCGTGAGCTGGAATAGCGGCGCTTTAACCTCCGGAGTGCACACCTTCCCC

GCTGTGCTCCAGTCCTCCGGTTTATACTCTTTATCCTCCGTGGTGACCGTGCCTTCCTC

CAGCCTCGGCACCAAGACCTACACTTGTAACGTGGACCACAAGCCCAGCAACACCA

AGGTGGACAAGAGGGTGGAGTCCAAGTACGGACCTCCTTGTCCCCCTTGCCCCGCCC

CCGAGGCCGCTGGCGGACCCTCCGTGTTCCTCTTCCCCCCCAAACCCAAGGACACTT

TAATGATCTCCCGGACCCCCGAAGTGACTTGTGTGGTGGTGGACGTGTCCCAAGAAG

ACCCCGAGGTGCAGTTTAACTGGTACGTGGATGGCGTGGAGGTGCACAACGCCAAG

ACCAAGCCTAGGGAGGAACAGTTCAACTCCACCTACCGGGTGGTGTCCGTGCTCACC

GTGCTGCATCAAGATTGGCTGAACGGCAAGGAGTACAAGTGCAAGGTGAGCAACAA

GGGACTGCCCAGCTCCATCGAGAAGACCATCAGCAAGGCCAAAGGCCAGCCCCGGG

AACCTCAAGTTTATACACTGCCCCCCAGCCAAGAAGAGATGACCAAGAACCAAGTTT

CTTTAACTTGTTTAGTGAAGGGCTTCTACCCTAGCGACATCGCTGTGGAGTGGGAGTC

CAATGGCCAGCCCGAAAACAATTATAAGACCACCCCCCCCGTGCTGGACTCCGATGG

TTCTTTTTTTTTATACTCCAAGCTGACAGTGGACAAGTCTCGTTGGCAAGAAGGCAAC

GTGTTCTCTTGTAGCGTGATGCACGAGGCTTTACACAACCACTACACCCAGAAGTCTT

TATCTCTGTCTTTAGGC.

(SEQ ID NO: 34)

CAAGTGCAGCTGGTTCAAAGTGGTGTTGAAGTTAAGAAGCCTGGAGCTAGTGTG

AAGGTGTCCTGTAAGGCCTCCGGCTATGCCTTTACAAACTACTGGCTCGGGTGGATGA

AGCAGCGCCCAGGACACGGTCTGGAATGGATTGGCGACTTTTACCCACGGACAGGA

AATACATTCTATAATGAAAACTTCAAAGGCAAAGTGACCATCACAGCCGATAAGTCCA

TTACCACTGCATACATGCAGCTCAGTAGTCTCAAAGCTAGTGATACAGCAGTGTATTA

CTGCGCCAGGGCCGGCACCGGGTTCGACTACTGGGGGCAGGGAACCACCCTCACCG

TGAGCTCTGCCAGCACCAAGGGCCCCAGCGTGTTCCCTCTGGCTCCTTGTAGCCGGT

CCACCTCCGAGTCCACAGCTGCTCTGGGCTGCCTCGTGAAGGACTACTTTCCCGAAC

CCGTTACCGTGAGCTGGAATAGCGGCGCTTTAACCTCCGGAGTGCACACCTTCCCCG

CTGTGCTCCAGTCCTCCGGTTTATACTCTTTATCCTCCGTGGTGACCGTGCCTTCCTCC

AGCCTCGGCACCAAGACCTACACTTGTAACGTGGACCACAAGCCCAGCAACACCAA

GGTGGACAAGAGGGTGGAGTCCAAGTACGGACCTCCTTGTCCCCCTTGCCCCGCCCC

CGAGGCCGCTGGCGGACCCTCCGTGTTCCTCTTCCCCCCCAAACCCAAGGACACTTT

AATGATCTCCCGGACCCCCGAAGTGACTTGTGTGGTGGTGGACGTGTCCCAAGAAGA

CCCCGAGGTGCAGTTTAACTGGTACGTGGATGGCGTGGAGGTGCACAACGCCAAGA

CCAAGCCTAGGGAGGAACAGTTCAACTCCACCTACCGGGTGGTGTCCGTGCTCACCG

TGCTGCATCAAGATTGGCTGAACGGCAAGGAGTACAAGTGCAAGGTGAGCAACAAG

GGACTGCCCAGCTCCATCGAGAAGACCATCAGCAAGGCCAAAGGCCAGCCCCGGGA

ACCTCAAGTTTATACACTGCCCCCCAGCCAAGAAGAGATGACCAAGAACCAAGTTTC

TTTAACTTGTTTAGTGAAGGGCTTCTACCCTAGCGACATCGCTGTGGAGTGGGAGTCC

-continued

AATGGCCAGCCCGAAAACAATTATAAGACCACCCCCCCCGTGCTGGACTCCGATGGT
TCTTTTTTTTTATACTCCAAGCTGACAGTGGACAAGTCTCGTTGGCAAGAAGGCAACG
TGTTCTCTTGTAGCGTGATGCACGAGGCTTTACACAACCACTACACCCAGAAGTCTTT
ATCTCTGTCTTTAGGC.

(SEQ ID NO: 35)
CAAGTCCAACTGGTTCAATCTGGCGTGGAAGTCAAGAAGCCCGGAGCCTCCGTG
AAGGTGAGCTGCAAGGCAAGCGGCTATGCATTCACTAACTACTGGCTCGGATGGGTG
AAACAACGGCCAGGACATGGCCTGGAATGGATCGGCGACTTCTACCCTAGGACTGGC
AACACTTTCTATAACGAGAACTTTAAGGGCAAGGTCACCATTACAGCTGATAAGAGTA
TCACTACCGCCTACATGCAGCTGTCTTCCCTGAAAGCTAGTGATACAGCCGTTTATTAC
TGTGCTCGGGCTGGCACAGGATTCGATTATTGGGGACAGGGTACCACACTCACAGTG
TCCTCTGCCAGCACCAAGGGCCCCAGCGTGTTCCCTCTGGCTCCTTGTAGCCGGTCC
ACCTCCGAGTCCACAGCTGCTCTGGGCTGCCTCGTGAAGGACTACTTTCCCGAACCC
GTTACCGTGAGCTGGAATAGCGGCGCTTTAACCTCCGGAGTGCACACCTTCCCCGCT
GTGCTCCAGTCCTCCGGTTTATACTCTTTATCCTCCGTGGTGACCGTGCCTTCCTCCAG
CCTCGGCACCAAGACCTACACTTGTAACGTGGACCACAAGCCCAGCAACACCAAGG
TGGACAAGAGGGTGGAGTCCAAGTACGGACCTCCTTGTCCCCCTTGCCCCGCCCCCG
AGGCCGCTGGCGGACCCTCCGTGTTCCTCTTCCCCCCCAAACCCAAGGACACTTTAA
TGATCTCCCGGACCCCCGAAGTGACTTGTGTGGTGGTGGACGTGTCCCAAGAAGACC
CCGAGGTGCAGTTTAACTGGTACGTGGATGGCGTGGAGGTGCACAACGCCAAGACC
AAGCCTAGGGAGGAACAGTTCAACTCCACCTACCGGGTGGTGTCCGTGCTCACCGTG
CTGCATCAAGATTGGCTGAACGGCAAGGAGTACAAGTGCAAGGTGAGCAACAAGGG
ACTGCCCAGCTCCATCGAGAAGACCATCAGCAAGGCCAAAGGCCAGCCCCGGGAAC
CTCAAGTTTATACACTGCCCCCCAGCCAAGAAGAGATGACCAAGAACCAAGTTTCTT
TAACTTGTTTAGTGAAGGGCTTCTACCCTAGCGACATCGCTGTGGAGTGGGAGTCCA
ATGGCCAGCCCGAAAACAATTATAAGACCACCCCCCCCGTGCTGGACTCCGATGGTT
CTTTTTTTTTATACTCCAAGCTGACAGTGGACAAGTCTCGTTGGCAAGAAGGCAACGT
GTTCTCTTGTAGCGTGATGCACGAGGCTTTACACAACCACTACACCCAGAAGTCTTTA
TCTCTGTCTTTAGGC.

(SEQ ID NO: 36)
CAAGTTCAGCTGGTGCAATCCGGTGTCGAGGTGAAGAAACCAGGCGCAAGCGT
GAAAGTCTCCTGCAAGGCTTCTGGCTATGCCTTCACTAACTACTGGCTCGGCTGGATG
AAGCAGAGGCCCGGACATGGGCTGGAGTGGATCGGAGACTTCTATCCCAGAACTGG
AAACACCTTTTACAACGAGAATTTCAAGGGCAAGGTCACCCTGACTGCCGACAAATC
CTCTAACACAGCTTACATGCAGCTGAGCAGTCTGACATCCGAAGACTCTGCAGTTTAC
CTGTGTGCTCGGGCAGGCACAGGCTTCGATTATTGGGGGCAAGGGACCACTCTGACT
GTGTCTTCCGCCAGCACCAAGGGCCCCAGCGTGTTCCCTCTGGCTCCTTGTAGCCGG
TCCACCTCCGAGTCCACAGCTGCTCTGGGCTGCCTCGTGAAGGACTACTTTCCCGAA
CCCGTTACCGTGAGCTGGAATAGCGGCGCTTTAACCTCCGGAGTGCACACCTTCCCC
GCTGTGCTCCAGTCCTCCGGTTTATACTCTTTATCCTCCGTGGTGACCGTGCCTTCCTC
CAGCCTCGGCACCAAGACCTACACTTGTAACGTGGACCACAAGCCCAGCAACACCA

-continued

AGGTGGACAAGAGGGTGGAGTCCAAGTACGGACCTCCTTGTCCCCCTTGCCCCGCCC

CCGAGGCCGCTGGCGGACCCTCCGTGTTCCTCTTCCCCCCCAAACCCAAGGACACTT

TAATGATCTCCCGGACCCCCGAAGTGACTTGTGTGGTGGTGGACGTGTCCCAAGAAG

ACCCCGAGGTGCAGTTTAACTGGTACGTGGATGGCGTGGAGGTGCACAACGCCAAG

ACCAAGCCTAGGGAGGAACAGTTCAACTCCACCTACCGGGTGGTGTCCGTGCTCACC

GTGCTGCATCAAGATTGGCTGAACGGCAAGGAGTACAAGTGCAAGGTGAGCAACAA

GGGACTGCCCAGCTCCATCGAGAAGACCATCAGCAAGGCCAAAGGCCAGCCCCGGG

AACCTCAAGTTTATACACTGCCCCCCAGCCAAGAAGAGATGACCAAGAACCAAGTTT

CTTTAACTTGTTTAGTGAAGGGCTTCTACCCTAGCGACATCGCTGTGGAGTGGGAGTC

CAATGGCCAGCCCGAAAACAATTATAAGACCACCCCCCCCGTGCTGGACTCCGATGG

TTCTTTTTTTTTATACTCCAAGCTGACAGTGGACAAGTCTCGTTGGCAAGAAGGCAAC

GTGTTCTCTTGTAGCGTGATGCACGAGGCTTTACACAACCACTACACCCAGAAGTCTT

TATCTCTGTCTTTAGGC.

(SEQ ID NO: 37)

GAGATCGTGATGACCCAGTCCCCAGCCACACTGAGCCTGTCTGTGGGAGAGAGG

GTGACCCTGTCTTGCAAGGCTTCCGAGAACGTGGGCGGCTACGTGAGCTGGTATCAG

CAGAAGCCCGACCAGTCTCCTAAGCTGCTGATCTACGGAGCCTCCAGCAGGCACACA

GGAGTGCCAGACCGGTTCACCGGATCCGGAAGCGAGACAGACTTCACCCTGACAAT

CTCTTCCGTGCAGGCTGAGGATCTGGCCGCTTATCATTGTGGCCAGAATTACATCTATC

CCTTCACCTTTGGCGGCGGCACAAAGCTGGAGATCAAGCGGACCGTGGCTGCCCCCT

CCGTGTTCATCTTCCCCCCTTCCGACGAGCAGCTGAAGTCCGGCACCGCTAGCGTGG

TGTGTTTACTGAACAACTTCTACCCTCGTGAGGCCAAGGTGCAGTGGAAGGTGGACA

ACGCTTTACAGTCCGGCAACTCCCAAGAATCCGTGACCGAGCAAGATTCCAAGGACT

CCACCTACTCTTTATCCTCCACTTTAACTTTATCCAAGGCCGACTACGAGAAGCACAA

GGTGTACGCTTGTGAGGTGACCCATCAAGGTTTATCCTCCCCCGTGACCAAGTCCTTC

AATCGTGGCGAGTGC.

(SEQ ID NO: 38)

GAGATCGTGATGACCCAGTCCCCAGCCACACTGAGCCTGTCTGTGGGAGAGAGG

GTGACCCTGTCTTGCAAGGCTTCCGAGAACGTGGGCGGCTACGTGAGCTGGTATCAG

CAGAAGCCCGACCAGTCTCCTAAGCTGCTGATCTACGGAGCCTCCAGCAGGGCTACA

GGAGTGCCAGACCGGTTCACCGGATCCGGAAGCGAGACAGACTTCACCCTGACAAT

CTCTTCCGTGCAGGCCGAGGATCTGGCCGCTTATCACTGTGGCCAGAATTACATCTAT

CCCTTCACCTTTGGCGGCGGCACAAAGCTGGAGATCAAGCGGACCGTGGCTGCCCCC

TCCGTGTTCATCTTCCCCCCTTCCGACGAGCAGCTGAAGTCCGGCACCGCTAGCGTG

GTGTGTTTACTGAACAACTTCTACCCTCGTGAGGCCAAGGTGCAGTGGAAGGTGGAC

AACGCTTTACAGTCCGGCAACTCCCAAGAATCCGTGACCGAGCAAGATTCCAAGGAC

TCCACCTACTCTTTATCCTCCACTTTAACTTTATCCAAGGCCGACTACGAGAAGCACA

AGGTGTACGCTTGTGAGGTGACCCATCAAGGTTTATCCTCCCCCGTGACCAAGTCCTT

CAATCGTGGCGAGTGC.

(SEQ ID NO: 39)

GAGATCGTGATGACCCAGAGCCCTGCCACACTGAGCCTGTCTGTGGGCGAGAGG

GTGACCCTGTCCTGCAAGGCCTCCGAGAACGTGGGCGGCTACGTGTCTTGGTATCAG

-continued

CAGAAGCCCGACCAGTCCCCTAAGCTGCTGATCTACGGAGCCTCCAGCAGGCACACC

GGAGTGCCAGCTCGGTTCTCCGGAAGCGGATCTGGCACAGACTTTACCCTGACAATC

TCTTCCCTGGAGCCAGAGGATTTCGCCGTGTATCATTGTGGCCAGAATTACATCTATCC

CTTCACCTTTGGCGGCGGCACAAAGCTGGAGATCAAGCGGACCGTGGCTGCCCCCTC

CGTGTTCATCTTCCCCCCTTCCGACGAGCAGCTGAAGTCCGGCACCGCTAGCGTGGT

GTGTTTACTGAACAACTTCTACCCTCGTGAGGCCAAGGTGCAGTGGAAGGTGGACAA

CGCTTTACAGTCCGGCAACTCCCAAGAATCCGTGACCGAGCAAGATTCCAAGGACTC

CACCTACTCTTTATCCTCCACTTTAACTTTATCCAAGGCCGACTACGAGAAGCACAAG

GTGTACGCTTGTGAGGTGACCCATCAAGGTTTATCCTCCCCCGTGACCAAGTCCTTCA

ATCGTGGCGAGTGC.

(SEQ ID NO: 40)

GAAATTGTGCTGACTCAGTCTCCTGCTACTCTGTCCCTGTCTCCTGGTGAACGGG

CCACTCTGAGCTGCAAGGCCAGTGAAAATGTGGGTGGCTATGTTAGCTGGTATCAGC

AAAAGCCCGACCAGTCTCCCAAACTGCTGATCTACGGCGCTTCCAGTCGGCACACAG

GCGTGCCAGATCGCTTTACTGGGAGCGGCTCTGAGACTGACTTCACACTGACCATTA

GCAGTGTCCAGGCCGAAGATCTCGCAGCCTATCATTGCGGCCAGAACTACATCTATCC

ATTCACCTTCGGTGGAGGAACCAAACTGGAAATCAAGCGGACCGTGGCTGCCCCCTC

CGTGTTCATCTTCCCCCCTTCCGACGAGCAGCTGAAGTCCGGCACCGCTAGCGTGGT

GTGTTTACTGAACAACTTCTACCCTCGTGAGGCCAAGGTGCAGTGGAAGGTGGACAA

CGCTTTACAGTCCGGCAACTCCCAAGAATCCGTGACCGAGCAAGATTCCAAGGACTC

CACCTACTCTTTATCCTCCACTTTAACTTTATCCAAGGCCGACTACGAGAAGCACAAG

GTGTACGCTTGTGAGGTGACCCATCAAGGTTTATCCTCCCCCGTGACCAAGTCCTTCA

ATCGTGGCGAGTGC.

The nucleotide sequences shown in SEQ ID NO: 30-36 respectively encode heavy chains H1-H7, and the nucleotide sequences shown in SEQ ID NO: 37-40 respectively encode light chains L1-L4. The underlined parts encode heavy chain variable regions VH1~VH7, and light chain variable regions VL1~VL4, respectively.

In the third aspect of the present invention, the present invention provides an expression vector. According to an embodiment of the present invention, the expression vector carries the aforementioned nucleic acid molecule. After the expression vector according to the embodiment of the present invention is introduced into a suitable recipient cell, it can effectively realize the expression of the humanized antibody or its antigen-binding fragment that specifically recognizes TrkA under the mediation of the regulatory system, thereby realizing the large-scale in vitro acquisition of the humanized antibody or antigen-binding fragment.

According to an embodiment of the present invention, the aforementioned expression vector may further include at least one of the following additional technical features:

According to an embodiment of the present invention, the expression vector is a eukaryotic expression vector. Furthermore, the aforementioned humanized antibody or its antigen-binding fragment that specifically recognizes TrkA can be expressed in eukaryotic cells, such as CHO cells.

In the fourth aspect of the present invention, the present invention provides a recombinant cell. According to an embodiment of the present invention, the recombinant cell carries the aforementioned nucleic acid molecule, or expresses the aforementioned humanized antibody or antigen-binding fragment thereof. The recombinant cells according to the embodiments of the present invention can be used for in vitro expression and large-scale acquisition of the aforementioned humanized antibody or antigen-binding fragment thereof that specifically recognizes TrkA.

According to an embodiment of the present invention, the aforementioned recombinant cell may further include at least one of the following additional technical features:

According to an embodiment of the present invention, the recombinant cell is obtained by introducing the aforementioned expression vector into a host cell.

According to an embodiment of the present invention, wherein the expression vector is introduced into the host cell by electrotransduction.

According to an embodiment of the present invention, the recombinant cell is a eukaryotic cell.

According to an embodiment of the present invention, the recombinant cell is a mammalian cell.

In the fifth aspect of the present invention, the present invention provides a pharmaceutical composition. According to an embodiment of the present invention, the pharmaceutical composition comprises the aforementioned antibody, the aforementioned nucleic acid molecule, the aforementioned expression vector or the aforementioned recombinant cell. The humanized antibody or expressed humanized antibody contained in the pharmaceutical composition according to the embodiment of the present invention has the same in vivo and in vitro activities as the human-mouse chimeric anti-TrkA monoclonal antibody 23E12. It not only can specifically target and bind to TrkA receptor, block the binding of NGF and TrkA, effectively inhibit pain, basically without the characteristics of antibody-dependent cell-mediated cytotoxicity (ADCC), but also has lower immunogenicity and better pharmacokinetic parameters than the human-mouse chimeric anti-TrkA monoclonal antibody 23E12.

In the sixth aspect of the present invention, the present invention provides use of the aforementioned antibody, the aforementioned nucleic acid molecule, the aforementioned expression vector, the aforementioned recombinant cell, or the aforementioned pharmaceutical composition in the manufacture of a medicament for the treatment or prevention of pain, cancer, inflammation or inflammatory diseases, neurodegenerative diseases, Sjogren's syndrome, endometriosis, diabetic peripheral neuropathy, prostatitis, pelvic pain syndrome, and diseases related to the unbalanced regulation of bone remodeling, and diseases caused by abnormal signal conduction of connective tissue growth factor.

According to an embodiment of the present invention, the aforementioned use may further include at least one of the following additional technical features:

According to an embodiment of the present invention, the medicament is used to treat or prevent neuropathic pain, inflammatory pain, cancer-related pain, fracture-related pain, surgery-related pain, inflammatory lung disease, interstitial cystitis, painful bladder syndrome, inflammatory bowel disease, inflammatory skin disease, Raynaud's syndrome, idiopathic pulmonary fibrosis, scar (hypertrophy, keloid type and other forms), sclerosis, endocardial myocardial fibrosis, atrial fibrosis, bone marrow fibrosis, progressive massive fibrosis (lung), renal-derived systemic fibrosis, scleroderma, systemic sclerosis, joint fibrosis, ocular fibrosis, non-small cell lung cancer, papillary thyroid cancer, glioblastoma multiforme, colorectal cancer, melanoma, bile duct cancer or sarcoma, acute myeloid leukemia, large cell neuroendocrine cancer, neuroblastoma, prostate cancer, pancreatic cancer, melanoma, head and neck squamous cell carcinoma or gastric cancer.

In the sixth aspect of the present invention, the present invention provides a method of treating or preventing a disease caused by abnormal expression of NGF, abnormal expression of TrkA, or abnormal activity of TrkA in a subject comprising administering to the subject a therapeutically effective amount of the aforementioned antibody, the aforementioned nucleic acid molecule, the aforementioned expression vector, the aforementioned recombinant cell, or the aforementioned pharmaceutical composition.

According to an embodiment of the present invention, the disease caused by abnormal expression of NGF, abnormal expression of TrkA, or abnormal activity of TrkA includes neuropathic pain, inflammatory pain, cancer-related pain, fracture-related pain, surgery-related pain, inflammatory lung disease, interstitial cystitis, painful bladder syndrome, inflammatory bowel disease, inflammatory skin disease, Raynaud's syndrome, idiopathic pulmonary fibrosis, scar (hypertrophy, keloid type and other forms), sclerosis, endocardial myocardial fibrosis, atrial fibrosis, bone marrow fibrosis, progressive massive fibrosis (lung), renal-derived systemic fibrosis, scleroderma, systemic sclerosis, joint fibrosis, ocular fibrosis, non-small cell lung cancer, papillary thyroid cancer, glioblastoma multiforme, colorectal cancer, melanoma, bile duct cancer or sarcoma, acute myeloid leukemia, large cell neuroendocrine cancer, neuroblastoma, prostate cancer, pancreatic cancer, melanoma, head and neck squamous cell carcinoma or gastric cancer.

In the sixth aspect of the present invention, the present invention provides the aforementioned antibody, the aforementioned nucleic acid molecule, the aforementioned expression vector, the aforementioned recombinant cell, or the aforementioned pharmaceutical composition for use in treating or preventing a disease caused by abnormal expression of NGF, abnormal expression of TrkA, or abnormal activity of TrkA in a subject.

According to an embodiment of the present invention, the present invention provides the aforementioned antibody, the aforementioned nucleic acid molecule, the aforementioned expression vector, the aforementioned recombinant cell, or the aforementioned pharmaceutical composition for use in treating or preventing a disease caused by abnormal expression of NGF, abnormal expression of TrkA, or abnormal activity of TrkA in a subject, wherein the disease caused by abnormal expression of NGF, abnormal expression of TrkA, or abnormal activity of TrkA includes neuropathic pain, inflammatory pain, cancer-related pain, fracture-related pain, surgery-related pain, inflammatory lung disease, interstitial cystitis, painful bladder syndrome, inflammatory bowel disease, inflammatory skin disease, Raynaud's syndrome, idiopathic pulmonary fibrosis, scar (hypertrophy, keloid type and other forms), sclerosis, endocardial myocardial fibrosis, atrial fibrosis, bone marrow fibrosis, progressive massive fibrosis (lung), renal-derived systemic fibrosis, scleroderma, systemic sclerosis, joint fibrosis, ocular fibrosis, non-small cell lung cancer, papillary thyroid cancer, glioblastoma multiforme, colorectal cancer, melanoma, bile duct cancer or sarcoma, acute myeloid leukemia, large cell neuroendocrine cancer, neuroblastoma, prostate cancer, pancreatic cancer, melanoma, head and neck squamous cell carcinoma or gastric cancer.

In the seventh aspect of the present invention, the present invention provides a kit for detecting TrkA. According to an embodiment of the present invention, the kit includes any one of the aforementioned antibodies. The aforementioned TrkA antibody can specifically target and bind to TrkA. The kit according to the embodiment of the present invention can realize the specific detection of TrkA. For example, when the antibody is bound with a fluorescent group, a fluorescent detection device can be used to realize the localization or real-time detection of TrkA.

In the eighth aspect of the present invention, the present invention provides use of the aforementioned antibody, the aforementioned nucleic acid molecule, the aforementioned expression vector or the aforementioned recombinant cell in the preparation of a kit for detecting TrkA or diagnosing a TrkA-related disease.

In the eighth aspect of the present invention, the present invention provides a method of detecting TrkA or diagnosing a TrkA-related disease in a subject using a kit comprising the aforementioned antibody, the aforementioned nucleic acid molecule, the aforementioned expression vector or the aforementioned recombinant cell.

In the eighth aspect of the present invention, the present invention provides the aforementioned antibody, the aforementioned nucleic acid molecule, the aforementioned expression vector or the aforementioned recombinant cell for use in the preparation of a kit for detecting TrkA or diagnosing a TrkA-related disease.

EXAMPLES

Figure 1:
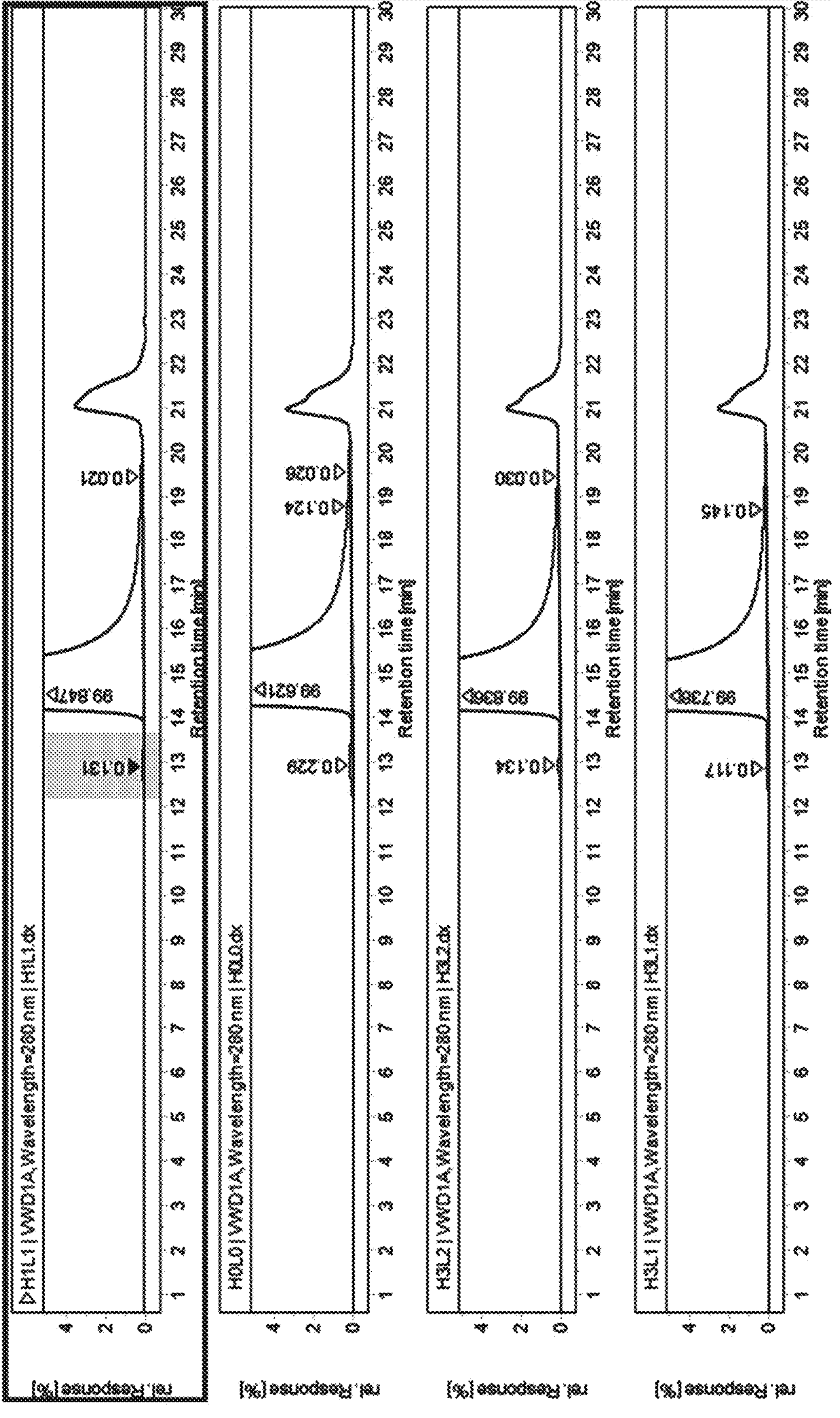
FIG. 1 is a diagram showing the results of the purity of monomer of humanized antibodies evaluated by the SEC-HPLC purity detection method according to an embodiment of the present invention.

The embodiments of the present invention are described in detail below. Examples of the embodiments are shown in the accompanying drawings, wherein the same or similar reference numerals represent the same or similar elements or elements having the same or similar functions throughout. The embodiments described below with reference to the drawings are exemplary and are intended to explain the present invention, but should not be construed as limiting the present invention.

In the course of describing the present invention, the terms used herein are explained. These explanations are only for the convenience of understanding the scheme, and should not be regarded as limiting the protection scheme of the present invention.

Antibody

As used herein, the term "antibody" is an immunoglobulin molecule capable of binding to a specific antigen. It consists of two light chains with a lighter molecular weight and two heavy chains with a heavier molecular weight. The heavy (H) and light (L) chains are linked by disulfide bonds to form a tetrapeptide chain molecule. Among them, the amino acid sequence of the amino terminal (N-terminal) of the peptide chain changes greatly, which is called the variable region (V region). The carboxyl terminal (C-terminal) is relatively stable with little change, which is called the constant region (C region). The constant region of the antibody can mediate the binding of the immunoglobulin to host tissues or factors. The host tissues or factors include various cells of the immune system (for example, effector cells) and the first component of the classical complement system (C1q). The V regions of the L and H chains are referred to as VL and VH, respectively.

In the variable region, the amino acid composition and arrangement order of certain regions have a higher degree of variation, which is called the hypervariable region (Hypervariable region, HVR). Hypervariable region is where antigen and antibody binds, so it is also called complementarity-determining region (CDR). They are interspersed in more conserved regions of the called framework regions (FR). Each VH and VL can be composed of three CDRs and four FR regions, which can be arranged in the following order from the amino terminus to the carboxy terminus: FR1, CDR1, FR2, CDR2, FR3, CDR3, and FR4.

The present invention utilizes the extracellular segment of TrkA to obtain anti-TrkA Fab (antigen-binding fragment) antibody fragments with high specificity and high affinity through immunization. The antibody fragment can specifically bind to the TrkA antigen, which can target the treatment of diseases such as pain or tumors.

In some embodiments, the present invention provides a humanized antibody or antigen-binding fragment, wherein the humanized antibody or antigen-binding fragment thereof comprises a heavy chain variable region with the amino acid sequence shown in any one of SEQ ID NO: 2-8, and a light chain variable region with the amino acid sequence shown in any one of SEQ ID NO: 10-13. The inventors can obtain the CDR region of the heavy chain variable region sequence and the CDR region of the light chain variable region sequence through the antibody sequence alignment database (NCBI, IMGT). In other embodiments, the heavy chain variable region sequence of the antibody or antigen-binding fragment comprises conservative amino acid substitutions compared to the amino acid sequence shown in SEQ ID NO: 2-8. In some embodiments, the light chain variable region sequence of the antibody or antigen-binding fragment comprises conservative amino acid substitutions compared to the amino acid sequence shown in SEQ ID NO: 10-13. "Antigen-binding fragment" refers to an antibody fragment that retains the ability to specifically bind to an antigen (ROR2). Examples of antigen-binding fragments include, but are not limited to, at least one of Fv fragments, disulfide bond-stabilized Fv fragments (dsFv), Fab fragments, (Fab) 2 fragments, scFv-Fc fusion proteins, scFv-Fv fusion proteins, Fv-Fc fusion proteins, multispecific antibodies formed from antigen-binding fragments, single domain antibodies, domain antibodies, bivalent domain antibodies, or minimal recognition units. "Conservative amino acid substitution" refers to the substitution of an amino acid with a residue that is biologically, chemically or structurally similar to another amino acid. Of course, these conservative amino acid substitutions will not change the biological function of the antibody or antigen-binding fragment. In some specific ways, these conservative amino acid substitutions can occur on amino acids other than the CDR regions in the heavy chain variable region and the light chain variable region. Biological similarity means that the substitution does not destroy the TrkA antibody or biological activity with the TrkA antigen. Structural similarity refers to that amino acids have side chains of similar length, such as alanine, glycine, or serine, or side chains of similar size. Chemical similarity means that amino acids have the same charge or are both hydrophilic or hydrophobic. For example, the hydrophobic residues isoleucine, valine, leucine or methionine are substituted with each other. Alternatively, polar amino acids can be substituted for each other, such as lysine is substituted with arginine, aspartic acid is substituted with glutamic acid, asparagine is substituted with glutamine, threonine is substituted with serine, etc.

The term "murine antibody" usually refers to that the B cells derived from immunized mice are fused with myeloma cells, and then the mouse hybrid fusion cells that can proliferate immortally and secrete antibodies are screened, and then the antibody is screened, prepared and purified.

The term "chimeric antibody" refers to an antibody obtained by combining non-human genetic material with human genetic material. "Chimeric antibody" or "chimeric anti-TrkA antibody" herein includes antibodies in which the variable region sequence is derived from one species and the constant region sequence is derived from another species. For example, the variable region sequence is derived from a mouse antibody and the constant region sequence is derived from a human antibody.

The term "humanized antibody" refers to an antibody that is derived from a non-human species but whose protein sequence has been modified to increase its similarity to human naturally-occurring antibodies. Specifically, a humanized antibody refers to a molecule having an antigen binding site that is essentially derived from an immunoglobulin of a non-human species, wherein the remaining immunoglobulin structure of the molecule is based on the structure and/or sequence of a human immunoglobulin. The antigen binding site may comprise a complete variable domain fused to a constant domain or only a complementarity determining region (CDR) grafted to an appropriate framework region in the variable domain. The antigen binding site can be wild-type or modified by one or more amino acid substitutions, for example, modifications are made to be more similar to human immunoglobulins. Some forms of humanized antibodies retain all CDR sequences (e.g., a humanized mouse antibody that contains all six CDRs from a mouse antibody). Other forms have one or more CDRs that have changed relative to the original antibody.

In some preferred embodiments, the present invention provides a humanized anti-TrkA antibody. The antibody has a heavy chain with the amino acid sequence shown in any one of SEQ ID NO: 17-23 and a light chain with the amino acid sequence shown in any one of SEQ ID NO: 24-27.

In some preferred embodiments, the present invention provides a humanized anti-TrkA single chain antibody. The single-chain antibody comprises a heavy chain variable region with the amino acid sequence shown in any one of SEQ ID NO: 2-8 and a light chain variable region with the amino acid sequence shown in any one of SEQ ID NO: 10-13, wherein the C-terminus of the heavy chain variable region is connected to the N-terminus of the light chain variable region through a connecting peptide linker, or the C-terminus of the light chain variable region is connected to the N-terminus of the heavy chain variable region through a connecting peptide linker.

Nucleic Acid Molecule, Expression Vector, Recombinant Cell

In the process of preparing or obtaining these antibodies, nucleic acid molecules expressing these antibodies can be connected to different vectors and then expressed in different cells to obtain corresponding antibodies.

To this end, the present invention also provides an isolated nucleic acid molecule, which encodes the antibody or antigen-binding fragment described above.

In some embodiments, the isolated nucleic acid molecule comprises the nucleotide sequence shown in any one of SEQ ID NO: 30-36 or has the nucleotide sequence shown in any one of SEQ ID NO: 37-40.

In some embodiments, the isolated nucleic acid molecule comprises at least more than 90% homology with the nucleotide sequence shown in SEQ ID NO: 30-36, preferably has more than 95% homology, and more preferably comprises more than 98% and 99% homology. In at least some embodiments, the isolated polynucleotide comprises at least more than 90% homology with the nucleotide sequence shown in SEQ ID NO: 37-40, preferably comprises more than 95% homology, and more preferably comprises more than 98% and 99% homology. These sequences that comprise homology with the nucleotide sequences shown in SEQ ID NO: 30~36 or SEQ ID NO: 37~40 can express amino acid sequences similar to SEQ ID NO: 17~23 or SEQ ID NO: 24~27, so that they can specifically bind to the TrkA antigen to achieve the targeting function of the antibody.

In some preferred embodiments, the isolated nucleic acid molecule comprises the heavy chain nucleotide sequence shown in SEQ ID NO: 30~36 and the light chain nucleotide sequence shown in SEQ ID NO: 37~40. These nucleotide sequences are optimized for species and are more easily expressed in mammalian cells.

The present invention also provides an expression vector, which contains the aforementioned isolated nucleic acid molecule. When the aforementioned isolated polynucleotide is ligated to a vector, the polynucleotide can be directly or indirectly connected to control elements on the vector, as long as these control elements can control the translation and expression of the polynucleotide. Of course, these control elements can come directly from the vector itself, or they can be exogenous, that is, not from the vector itself. Of course, the polynucleotide may be operably linked to the control element. "Operably linked" herein refers to the connection of a exogenous gene to a vector, so that control elements in the vector, such as transcription control sequences and translation control sequences, can exert its expected function of regulating the transcription and translation of exogenous genes. Of course, the polynucleotides used to encode the heavy and light chains of the antibodies can be inserted into different vectors independently, and they are usually inserted into the same vector. Commonly used vectors can be, for example, plasmids, phages, and the like. For example, plasmid-X plasmid.

The invention also provides a recombinant cell, which contains the expression vector. The expression vector can be introduced into mammalian cells, constructed to obtain recombinant cells, and then these recombinant cells can be used to express the humanized antibodies or antigen-binding fragments provided by the present invention. By culturing the recombinant cells, corresponding antibodies can be obtained. These usable mammalian cells may be, for example, CHO cells and the like.

Pharmaceutical Composition, Kit and Pharmaceutical Uses and Uses in the Preparation of Kits The invention also provides a pharmaceutical composition, which comprises the antibody or antigen-binding fragment described above and a pharmaceutically acceptable carrier.

The anti-TrkA humanized antibodies provided herein can be incorporated into a pharmaceutical composition suitable for administration to a subject. Generally, these pharmaceutical compositions include the anti-TrkA humanized antibodies provided herein as well as a pharmaceutically acceptable carrier. A "pharmaceutically acceptable carrier" may include any and all solvents, dispersion media, coatings, antibacterial and antifungal agents, isotonic and delayed absorption agents, and the like that are physiologically compatible. Specific examples may be one or more of water, saline, phosphate buffered saline, glucose, glycerol, ethanol, and the like, and combinations thereof. In many cases, pharmaceutical compositions include isotonic agents, such as sugars, polyalcohols (such as mannitol, sorbitol), or sodium chloride. Of course, pharmaceutically acceptable carriers may also include minor amounts of auxiliary substances, such as wetting or emulsifying agents, preservatives or buffering agents, to extend the shelf life or efficacy of the antibody.

For example, the antibodies of the invention can be incorporated into pharmaceutical compositions suitable for parenteral administration (e.g., intravenous, subcutaneous, intraperitoneal, intramuscular). These pharmaceutical compositions can be prepared in various forms. Examples are liquid, semi-solid, and solid dosage forms, including, but not limited to, liquid solutions (e.g., injection solutions and infusion solutions), dispersing or suspending agents, tablets, pills, powders, liposomes, and suppositories. Typical pharmaceutical compositions are in the form of injection solutions or infusion solutions. The antibodies can be administered by intravenous infusion or injection or intramuscular or subcutaneous injection.

Of course, the anti-TrkA humanized antibodies herein can also be made into kits or part of other diagnostic reagents as needed. According to the embodiment of the present invention, the present invention also provides a kit comprising the above-mentioned TrkA antibody. The kit provided by the present invention can be used, for example, the kit can be used for immunoblotting, immunoprecipitation, etc., which involves detection using the specific binding properties of TrkA antigen and antibodies. These kits may include any one or more of the following: antagonists, anti-TrkA humanized antibodies or drug reference materials; protein purification columns; immunoglobulin affinity purification buffers; cell assay diluents; instructions or literature, etc. Anti-TrkA humanized antibodies can be used for different types of diagnostic tests, such as the detection of various diseases or the presence of drugs, toxins or other proteins in vitro or in vivo. For example, it can be used to test related diseases by testing the serum or blood of the subject. Such related diseases may include TrkA-related diseases such as pain, cancer, inflammation or inflammatory diseases, neurodegenerative diseases, Sjogren's syndrome, endometriosis, diabetic peripheral neuropathy, prostatitis, pelvic pain syndrome, and diseases related to the unbalanced regulation of bone remodeling, and diseases caused by abnormal signal conduction of connective tissue growth factor, and the like. Of course, the antibodies provided herein can also be used for radioimmunodetection and radioimmunotherapy of the above diseases.

Specifically, the aforementioned pain, inflammation or inflammatory disease, neurodegenerative diseases, Sjogren's syndrome, endometriosis, diabetic peripheral neuropathy, prostatitis, pelvic pain syndrome, diseases related to the regulation of bone remodeling imbalance and diseases caused by abnormal signaling of connective tissue growth factor include neuropathic pain, inflammatory pain, cancer-related pain, fracture-related pain, surgery-related pain, inflammatory lung disease, interstitial cystitis, painful bladder syndrome, inflammatory bowel disease, inflammatory skin disease, Raynaud's syndrome, idiopathic pulmonary fibrosis, scar (hypertrophy, keloid type and other forms), sclerosis, endocardial myocardial fibrosis, atrial fibrosis, bone marrow fibrosis, progressive massive fibrosis (lung), renal-derived systemic fibrosis, scleroderma, systemic sclerosis, joint fibrosis, ocular fibrosis.

These cancers or tumors can be any unregulated cell growth. Specifically, it may be non-small cell lung cancer, papillary thyroid cancer, glioblastoma multiforme, colorectal cancer, melanoma, bile duct cancer or sarcoma, acute myeloid leukemia, large cell neuroendocrine cancer, prostate cancer, neuroblastoma, pancreatic cancer, melanoma, head and neck squamous cell carcinoma or gastric cancer, etc.

When using the anti-TrkA humanized antibody provided by the present invention to treat the above-mentioned diseases, the anti-TrkA humanized antibody provided by the present invention may be provided to a subject. To this end, the present invention provides a method for treating the above-mentioned diseases, comprising administering an antibody or an antigen-binding fragment thereof provided by the present invention to a subject in need.

Example 1 Humanized Design of the Variable Region of the Murine Anti-TrKA Monoclonal Antibody 23E12

The immunogenicity analysis of the B cell epitope was carried out against the variable region of the murine anti-TrKA monoclonal antibody 23E12 by using the B cell epitope analysis software AbEpiMax, and the sequence of the antibody FR region with a strong B cell epitope was found.

Then, the sequence of the human antibody FR library that had high 3D structural homology with the original sequence and had a weaker B cell epitope was used to replace the sequence of the antibody FR region with a strong B cell epitope. The sequences of heavy and light chain variable region of the murine anti-TrKA monoclonal antibody 23E12 and modified heavy and light chain variable region of 23E12 were shown in Table 1.

TABLE 1

| | Heavy chain variable region | Sequence | Light chain variable region | Sequence |
|---|---|---|---|---|
| Variable region of the murine anti-TrKA monoclonal antibody 23E12 | VH0 | SEQ ID NO: 1 | VL0 | SEQ ID NO: 9 |
| Variable region of the humanized anti-TrKA monoclonal antibody 23E12 modified | VH1 | SEQ ID NO: 2 | VL1 | SEQ ID NO: 10 |
| | VH2 | SEQ ID NO: 3 | VL2 | SEQ ID NO: 11 |
| | VH3 | SEQ ID NO: 4 | VL3 | SEQ ID NO: 12 |
| | VH4 | SEQ ID NO: 5 | VL4 | SEQ ID NO: 13 |
| | VH5 | SEQ ID NO: 6 | | |
| | VH6 | SEQ ID NO: 7 | | |
| | VH7 | SEQ ID NO: 8 | | |

Example 2 Construction of Vector

A series of humanized antibody expression vectors (H1L1-IgG4, H3L1-IgG4, H3L2-IgG4) were constructed by molecular cloning, and the humanized antibody was expressed recombinantly in the CHO expression system. Nucleotide sequences encoding a series of humanized monoclonal antibody light and heavy chains (H1L1-IgG4, H3L1-IgG4, H3L2-IgG4) were obtained by entrusting GenScript Biotechnology Co., Ltd. through chemical synthesis. After the sequences were double digested, they were inserted between the same restriction sites of the eukaryotic expression vector to construct a series of humanized monoclonal antibody expression vectors (H1L1-IgG4, H3L1-IgG4, H3L2-IgG4). Then a series of verified and correct expression vectors were extracted by Invitrogen plasmid extraction kit, linearized with restriction enzymes, purified and recovered, and then stored at −20° C.

Example 3 Transfection of Vector Encoding a Series of Humanized Antibodies and Expression in Cells After the CHO host cells were resuscitated and cultured with CD CHO medium, the cells were collected for transfection when the density of the cells was about $8*10^5$ cell/mL. The transfected cells were about $1*10^7$ cell, the vector was about 40 μg, and the transfection method is by electroporation (Bio-Rad, Gene pulser Xcell). After the electric shock, the cells were cultured in 20 mL CD CHO medium. On the second day of culture, the cells were collected by centrifugation and resuspended in 20 mL CD CHO medium added with MSX to a final concentration of 50 μM. When the density of the cells was about $0.6*10^6$ cell/mL, the obtained mixed clones were passaged with CD CHO medium, and the density of the cells was about $0.2*10^6$ cell/mL. When the survival rate of the cells was about 90%, the cell culture fluid was collected.

Example 4 Collection of Cell Fermentation Broth and Purification of Humanized Antibody A series of humanized monoclonal antibodies were tested at the translation level. The collected cell culture fluid was purified by a Protein A chromatography column, and the absorption peak was collected for mass spectrometry. Mass spectrometry detected that a series of chimeric antibodies had a molecular weight of about 150 KD, which was consistent with the theoretical molecular weight and was in the form of a dimer. At the same time, the collected samples were detected by 10% SDS-PAGE electrophoresis after reduction and non-reduction, respectively. The reduced SDS-PAGE electrophoresis pattern showed two bands, about 25 KD and 50 KD, respectively. The non-reduced SDS-PAGE electrophoresis pattern showed a single band, around 150 KD. The band size of the electrophoresis pattern was consistent with the theory. After purification, the sample was dialyzed overnight at 4° C. with a 0.01M PBS buffer of pH 7.0.

Example 5 Evaluation of the Purity of Monomer of Humanized Antibodies by the SEC-HPLC Purity Detection Method The humanized antibody (H1L1-IgG4, H3L1-IgG4, H3L2-IgG4) samples and the chimeric antibody (H0L0-IgG4) samples were centrifuged. About 80 μg of the supernatant was taken and injected into HPLC for detection. The monomer peak area percentage of the humanized antibody was detected by SEC-HPLC. The higher the peak area percentage, the higher the purity of the monomer. The results were shown in FIG. 1. The results in the FIG. 1 showed that the monomer peak area percentages of the humanized antibodies H1L1-IgG4, H3L1-IgG4, and H3L2-IgG4 were 99.847%, 99.738%, and 99.836%, respectively, and the monomer peak area percentage of the chimeric antibody H0L0-IgG4 was 99.621%. It showed that the humanized antibodies H1L1-IgG4, H3L1-IgG4, H3L2-IgG4 and the chimeric antibody H0L0-IgG4 had high monomer purity.

Figure 2:
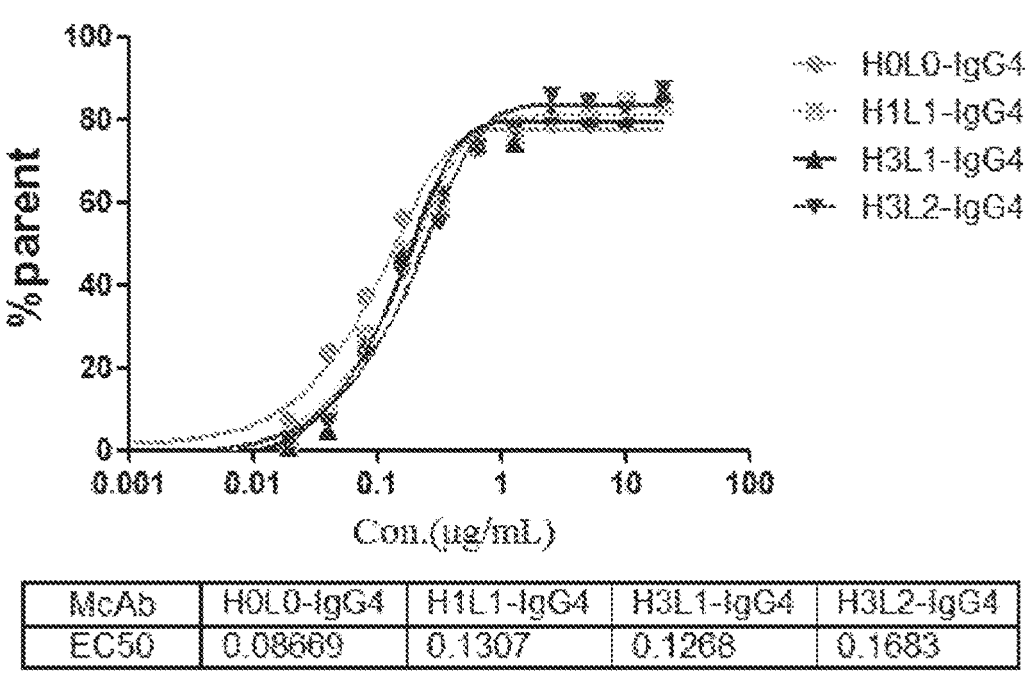
FIG. 2 is a diagram showing the experimental results of the binding ability of humanized antibodies and Human-TrKA detected by flow cytometry according to an embodiment of the present invention.

Example 6 Evaluation of the Binding Ability of Humanized Antibodies and Human-TrKA by Flow Cytometry Lentiviral technology was used to construct HEK293T-HumanTrkA cell model. The humanized antibody (H1L1-IgG4, H3L1-IgG4, H3L2-IgG4) samples and the chimeric antibody (H0L0-IgG4) samples were diluted with PBS buffer to 11 concentration gradients (20 μg/mL, 10 μg/mL, 5 μg/mL, 2.5 μg/mL, 1.25 μg/mL, 0.625 μg/mL, 0.313 μg/mL, 0.156 μg/mL, 0.078 μg/mL, 0.039 μg/mL, 0.019 μg/mL). Flow cytometry was used to detect the binding of each concentration gradient humanized antibody to the Human-TrKA receptor on the surface of HEK293T-HumanTrKA cells, and the binding ability of each humanized antibody to Human-TrKA was evaluated at the cellular level. The results were shown in FIG. 2. In the FIG. 2, the EC50 (half binding concentration) value reflected the binding ability of the antibody to Human-TrKA; the smaller the EC50 value, the stronger the binding ability of the antibody to Human-TrKA, and the higher the affinity of the antibody. It was generally believed that the EC50 value of high-affinity antibodies was lower than 1.5 μg/mL. The results in the FIG. 2 showed that the EC50 values of the humanized antibodies H1L1-IgG4, H3L1-IgG4, and H3L2-IgG4 were 0.1307 μg/mL, 0.1268 μg/mL, 0.1683 μg/mL, respectively, and the EC50 value of chimeric antibody H0L0-IgG4 was 0.08669 μg/mL. It showed that the humanized antibodies H1L1-IgG4, H3L1-IgG4, H3L2-IgG4 and the chimeric antibody H0L0-IgG4 had strong binding abilities to Human-TrKA; compared with the chimeric antibody H0L0-IgG4, the affinity of humanized antibodies H1L1-IgG4, H3L1-IgG4, H3L2-IgG4 binding to Human-TrKA remained basically unchanged.

Figure 3:
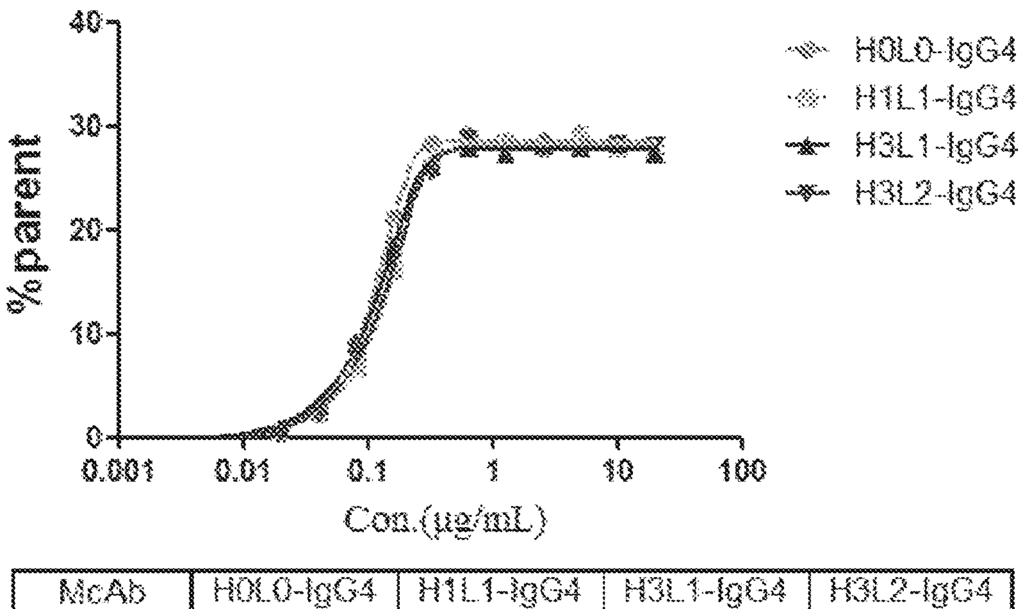
FIG. 3 is a diagram showing the experimental results of the binding ability of humanized antibodies and Mouse-TrKA detected by flow cytometry according to an embodiment of the present invention.

Example 7 Evaluation of the Binding Ability of Humanized Antibodies and Mouse-TrKA by Flow Cytometry Lentiviral technology was used to construct HEK293T-MouseTrkA cell model. The humanized antibody (H1L1-IgG4, H3L1-IgG4, H3L2-IgG4) samples and the chimeric antibody (H0L0-IgG4) samples were diluted with PBS buffer to 11 concentration gradients (20 μg/mL, 10 μg/mL, 5 μg/mL, 2.5 μg/mL, 1.25 μg/mL, 0.625 μg/mL, 0.313 μg/mL, 0.156 μg/mL, 0.078 μg/mL, 0.039 μg/mL, 0.019 μg/mL). Flow cytometry was used to detect the binding of each concentration gradient humanized antibody to the Human-TrKA receptor on the surface of HEK293T-MouseTrKA cells, and the binding ability of each humanized antibody to Mouse-TrKA was evaluated at the cellular level. The results were shown in FIG. 3. In the FIG. 3, the EC50 (half binding concentration) value reflected the binding ability of the antibody to Mouse-TrKA; the smaller the EC50 value, the stronger the binding ability of the antibody to Mouse-TrKA, and the higher the affinity of the antibody. It was generally believed that the EC50 value of high-affinity antibodies was lower than 1.5 μg/mL. The results in the FIG. 3 showed that the EC50 values of the humanized antibodies H1L1-IgG4, H3L1-IgG4, and H3L2-IgG4 were 0.1341 μg/mL, 0.1110

μg/mL, 0.1254 μg/mL, respectively, and the EC50 value of chimeric antibody H0L0-IgG4 was 0.1048 μg/mL. It showed that the humanized antibodies H1L1-IgG4, H3L1-IgG4, H3L2-IgG4 and the chimeric antibody H0L0-IgG4 had strong binding abilities to Mouse-TrKA; compared with the chimeric antibody H0L0-IgG4, the affinity of humanized antibodies H1L1-IgG4, H3L1-IgG4, H3L2-IgG4 binding to Mouse-TrKA remained basically unchanged.

Figure 4:
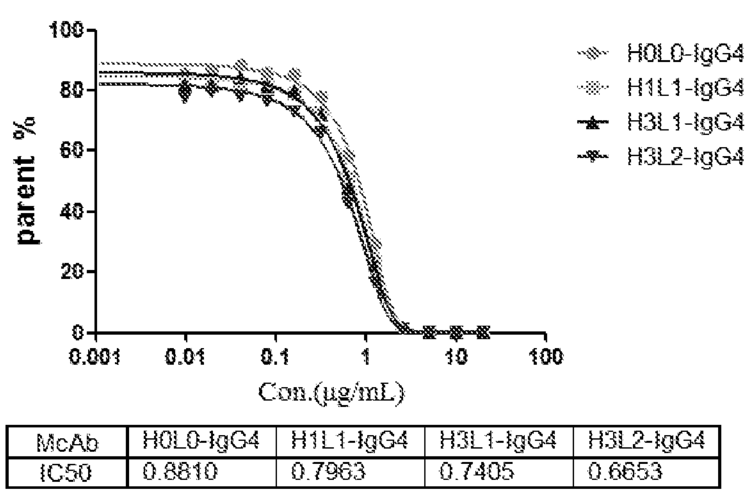
FIG. 4 is a diagram showing the results of the inhibitory effect of humanized antibodies on the binding of Human-NGF and Human-TrKA detected by flow cytometry according to an embodiment of the present invention.

Example 8 the Inhibitory Effect of Humanized Antibodies on the Binding of Human-NGF and Human-TrKA Detected by Flow Cytometry Human-NGF was biotinylated, and Human-NGF could bind to the extracellular region of Human-TrkA protein on HEK293T-HumanTrkA cells, and anti-TrkA monoclonal antibodies could also bind to the extracellular region of Human-TrkA protein on HEK293T-HumanTrkA cells. Competitive experiments were designed to detect the binding of Human-NGF to the extracellular region of Human-TrkA protein on HEK293T-HumanTrkA cells under the action of different concentrations (20 μg/mL, 10 μg/mL, 5 μg/mL, 2.5 μg/mL, 1.25 μg/mL, 0.625 μg/mL, 0.313 μg/mL, 0.156 μg/mL, 0.078 μg/mL, 0.039 μg/mL, 0.019 μg/mL) of humanized antibodies (H1L1-IgG4, H3L1-IgG4, H3L2-IgG4) and chimeric antibodies (H0L0-IgG4) by flow cytometry, and to study the inhibitory effect of each humanized antibody on the binding of Human-NGF and Human-TrKA. The experimental results were shown in FIG. 4. In the FIG. 4, the parent % value reflected the Human-NGF signal that bound to the extracellular region of the Human-TrKA protein on HEK293T-HumanTrkA cells. The lower the reading, the weaker the Human-NGF signal that bound to the extracellular region of the Human-TrkA protein on HEK293T-HumanTrkA cells, and the greater the effect of the antibody in inhibiting the binding of Human-NGF and Human-TrKA; as shown in the FIG. 4, as the concentrations of each humanized antibody (H1L1-IgG4, H3L1-IgG4, H3L2-IgG4) and chimeric antibody (H0L0-IgG4) increased, the parent % value gradually decreased until it approached zero, that is, the Human-NGF signal that bound to the extracellular region of the Human-TrkA protein gradually decreased until there was no Human-NGF to bind to the extracellular region of Human-TrkA protein, and the binding of Human-NGF to Human-TrkA was completely inhibited. The IC50 of the humanized antibodies (H1L1-IgG4, H3L1-IgG4, H3L2-IgG4) were 0.7963 μg/mL, 0.7405 μg/mL, 0.6653 μg/mL, respectively, and the IC50 of the chimeric antibody (H0L0-IgG4) was 0.8810 μg/mL; it could be seen that each humanized antibody (H1L1-IgG4, H3L1-IgG4, H3L2-IgG4) and chimeric antibody (H0L0-IgG4) could dose-dependently inhibit the binding of Human-NGF and Human-TrkA at the cellular level within a concentration range; compared with the chimeric antibody (H0L0-IgG4), the inhibitory effect of humanized antibodies (H1L1-IgG4, H3L1-IgG4, H3L2-IgG4) on the binding of Human-NGF and Human-TrKA remained basically unchanged.

Figure 5:
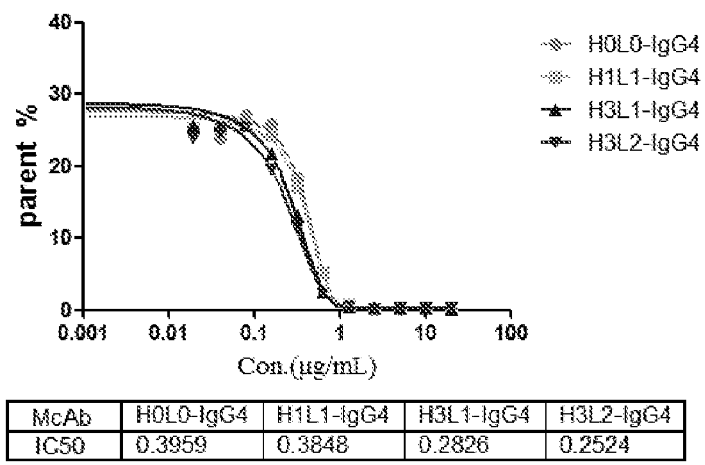
FIG. 5 is a diagram showing the results of the inhibitory effect of humanized antibodies on the binding of Mouse-NGF and Mouse-TrKA detected by flow cytometry according to an embodiment of the present invention.
Figure 6A:
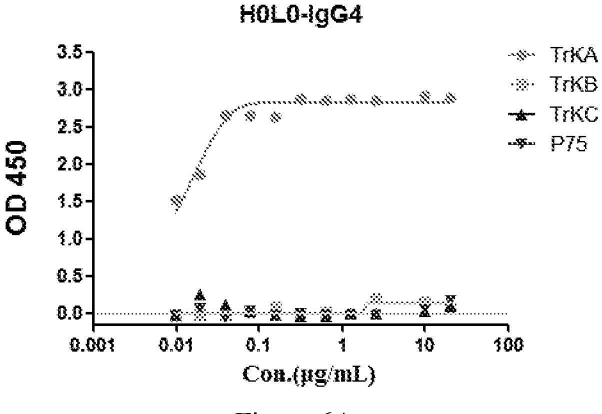
FIG. 6A-6D are diagrams showing the results of the specificity of the binding of humanized antibodies to the target Human-TrKA detected by flow cytometry according to an embodiment of the present invention.
Figure 6B:
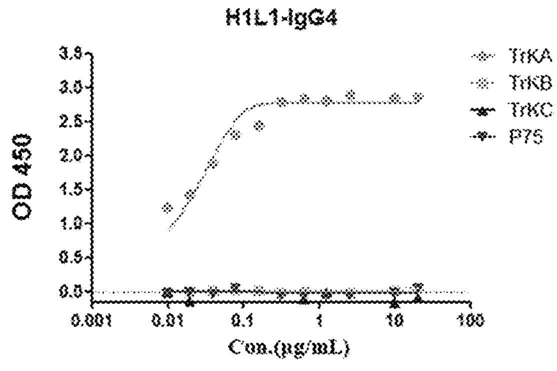
Figure 6C:
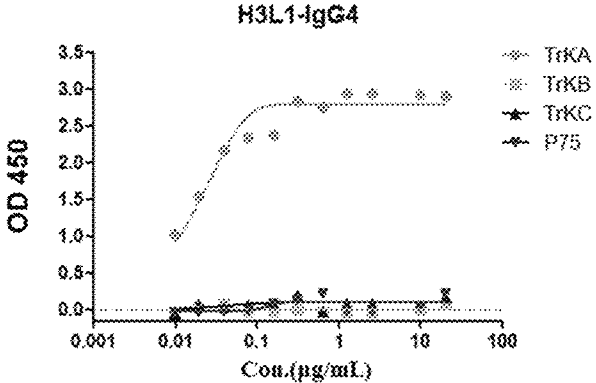
Figure 6D:
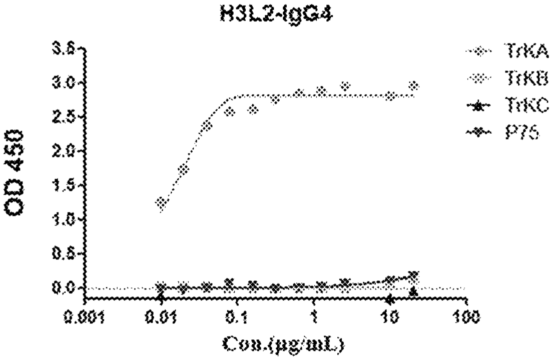

Example 9 The Inhibitory Effect of Humanized Antibodies on the Binding of Mouse-NGF and Mouse-TrKA Detected by Flow Cytometry Mouse-NGF was biotinylated, and Mouse-NGF could bind to the extracellular region of Mouse-TrkA protein on HEK293T-MouseTrkA cells, and anti-TrkA monoclonal antibodies could also bind to the extracellular region of Mouse-TrkA protein on HEK293T-MouseTrkA cells. Competitive experiments were designed to detect the binding of Mouse-NGF to the extracellular region of Mouse-TrkA protein on HEK293T-MouseTrkA cells under the action of different concentrations (20 μg/mL, 10 μg/mL, 5 μg/mL, 2.5 μg/mL, 1.25 μg/mL, 0.625 μg/mL, 0.313 μg/mL, 0.156 μg/mL, 0.078 μg/mL, 0.039 μg/mL, 0.019 μg/mL) of humanized antibodies (H1L1-IgG4, H3L1-IgG4, H3L2-IgG4) and chimeric antibodies (H0L0-IgG4) by flow cytometry, and to study the inhibitory effect of each humanized antibody on the binding of Mouse-NGF and Mouse-TrKA. The experimental results were shown in FIG. 5. In the FIG. 5, the parent % value reflected the Mouse-NGF signal that bound to the extracellular region of the Mouse-TrKA protein on HEK293T-MouseTrkA cells. The lower the reading, the weaker the Mouse-NGF signal that bound to the extracellular region of the Mouse-TrkA protein on HEK293T-MouseTrkA cells, and the greater the effect of the antibody in inhibiting the binding of Mouse-NGF and Mouse-TrKA; as shown in the FIG. 5, as the concentrations of each humanized antibody (H1L1-IgG4, H3L1-IgG4, H3L2-IgG4) and chimeric antibody (H0L0-IgG4) increased, the parent % value gradually decreased until it approached zero, that is, the Mouse-NGF signal that bound to the extracellular region of the Mouse-TrkA protein gradually decreased until there was no Mouse-NGF to bind to the extracellular region of Mouse-TrkA protein, and the binding of Mouse-NGF to Mouse-TrkA was completely inhibited. The IC50 of the humanized antibodies (H1L1-IgG4, H3L1-IgG4, H3L2-IgG4) were 0.3848 μg/mL, 0.2826 μg/mL, 0.2524 μg/mL, respectively, and the IC50 of the chimeric antibody (H0L0-IgG4) was 0.3959 μg/mL; it could be seen that each humanized antibody (H1L1-IgG4, H3L1-IgG4, H3L2-IgG4) and chimeric antibody (H0L0-IgG4) could dose-dependently inhibit the binding of Mouse-NGF and Mouse-TrkA at the cellular level within a concentration range; compared with the chimeric antibody (H0L0-IgG4), the inhibitory effect of humanized antibodies (H1L1-IgG4, H3L1-IgG4, H3L2-IgG4) on the binding of Mouse-NGF and Mouse-TrKA remained basically unchanged.

Example 10 Evaluation of the Specificity of Humanized Antibody Binding to the Target Human-TrKA by ELISA Method The TrkA receptor family belonged to receptor tyrosine kinases (RTKs), including TrkA, TrkB, and TrkC, which had high homology. TrkA was a receptor tyrosine kinase of nerve growth factor (NGF) that selectively bound to NGF and was a functional receptor for NGF. In addition to the high-affinity receptor TrkA, NGF could also bind to its low-affinity receptor p75. In the test, the binding of different concentrations (20 μg/mL, 10 μg/mL, 5 μg/mL, 2.5 μg/mL, 1.25 μg/mL, 0.625 μg/mL, 0.313 μg/mL, 0.156 μg/mL, 0.078 μg/mL, 0.039 μg/mL, 0.019 μg/mL) of humanized antibodies (H1L1-IgG4, H3L1-IgG4, H3L2-IgG4) and chimeric antibody (H0L0-IgG4) to TrKA, TrKB, TrKC, and P75 was detected by the ELISA method respectively, and the specificity of the binding of the tested antibody to the target Human-TrKA was evaluated. The results were shown in FIG. 6. In the FIG. 6, at a certain concentration of the antibody, the OD450 value reflected the strength of the binding between the antibody and the protein. The larger the reading, the stronger the binding between the antibody and the protein. The experimental results showed that humanized antibodies (H1L1-IgG4, H3L1-IgG4, H3L2-IgG4) and chimeric antibody (H0L0-IgG4) had good binding to TrKA receptors (The concentration of the tested antibody increased from 0 μg/mL to 20 μg/mL, and the OD450 value gradually increased until it approaches stable, close to about 3), and basically did not bind to TrKB, TrKC, P75 (the concentration of each tested antibody increased from 0 μg/mL to 20 μg/mL, the OD450 value was basically unchanged, close to 0). It could be seen that the specificity of the tested antibody binding to the target Human-TrKA was very good.

Figure 7:
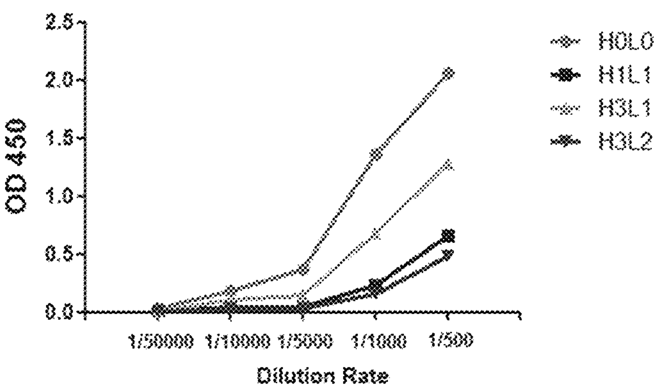
FIG. 7 is a diagram showing the results of ADA of humanized antibodies in mice evaluated by the ELISA method according to an embodiment of the present invention.

Example 11 Evaluation of ADA of Humanized Antibodies in Mice Evaluated by the ELISA Method In the test, 5 mice were immunized with humanized antibodies (H1L1-IgG4, H3L1-IgG4, H3L2-IgG4) and chimeric antibody (H0L0-IgG4) respectively, and tail vein blood was collected on the 14th day after administration. Each humanized antibody (H1L1-IgG4, H3L1-IgG4, H3L2-IgG4) and chimeric antibody (H0L0-IgG4) were diluted to 1 μg/mL coated microplate with PBS, 100 μL of which was added to each well and reacted at 4° C. overnight; the plate was washed 3 times with PBS solution, and blocked with 5% milk-PBS for 1 hr at room temperature; then the plate was washed once with PBS solution; 5% Milk-PBS buffer was used to gradiently dilute mouse tail vein blood (1:500, 1:1000, 1:5000, 1:10000, 1:50000), and the mouse tail vein blood was placed at room temperature for 1 hr, and then the pre-reacted tail vein blood was added to the microplate with 100 μL per well. A negative control (NC) was set. The mixture was reacted at room temperature for 1 hr, then the plate was washed 3 times with PBS solution and patted dry. 1:2000 diluted HRP-labeled goat anti-mouse IgG (Fc) secondary antibody was added, and reacted at room temperature for 1 hr; the plate was washed 5 times with PBS solution and patted dry, then 100 μL of substrate color developing solution TMB was added, and reacted for 20 min under dark conditions at room temperature; then 50 μL of stop solution was added and the OD450 value was read on the microplate reader after mixing. The results were shown in FIG. 7 below. In the FIG. 7, the OD450 value reflected the strength of the generated ADA. The larger the reading, the stronger the generated ADA. The experimental results showed that compared with chimeric antibodies (H0L0-IgG4), humanized antibodies (H1L1-IgG4, H3L1-IgG4, H3L2-IgG4) produced weaker ADA; it could be seen that humanized antibodies (H1L1-IgG4, H3L1-IgG4, H3L2-IgG4) had lower immunogenicity than chimeric antibodies (H0L0-IgG4).

Figure 8:
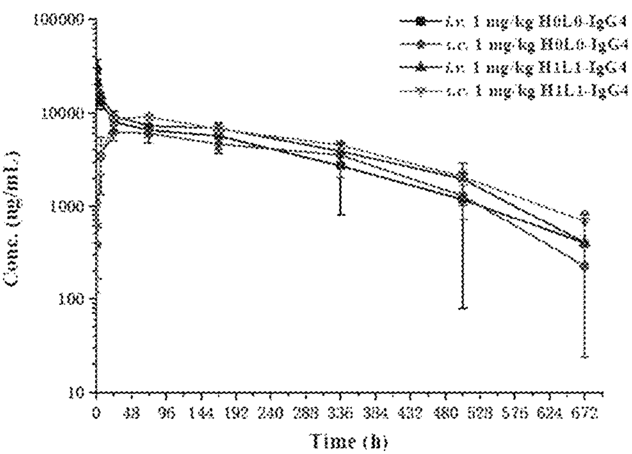
FIG. 8 is a diagram showing the results of pharmacokinetics of humanized antibodies in mice evaluated by the ELISA method according to an embodiment of the present invention.

Example 12 Evaluation of the Pharmacokinetics of Humanized Antibodies in Mice Evaluated by the ELISA Method 12 Male ICR mice were randomly divided into 4 groups and 3 mice/group. The chimeric antibody H0L0-IgG4 and humanized antibody H1L1-IgG4 were injected intravenously or subcutaneously at 1 mg/kg. Blood was collected at 1, 6, 24, 72, 168, 336, 504, and 672 h after administration, and plasma was separated (EDTA-K2 anticoagulation). In the intravenous administration group, blood was collected for an additional 0.25 h. The indirect ECLA method was used to analyze the concentration of H0L0-IgG4 or H1L1-IgG4 in each sample. The pharmacokinetic parameters were calculated based on the plasma drug concentration. The main PK parameter results were shown in Table 2, and the drug-time curve was shown in FIG. 8. The results showed that after intravenous injection of H0L0-IgG4 or H1L1-IgG4 in ICR mice, the average plasma half-life was 97 h and 143 h, respectively; after subcutaneous injection of H0L0-IgG4 or H1L1-IgG4, the average peak time was 40 h and 56 h, the average Cmax was 6.61 μg/mL and 9.49 μg/mL, the average AUClast was 2120 μg·h/mL and 3020 μg·h/mL, the average plasma half-life was 75 h and 122 h, and the absolute bioavailability was 89% and 101%, respectively. It could be seen that the humanized antibody H1L1-IgG4 had better pharmacokinetic parameters in mice compared with the chimeric antibody H0L0-IgG4.

TABLE 2

| Group | Tested substance | batch number | Mode of administration | dose mg/kg | $t_{1/2}$ h | $T_{max}$ h | $C_{max}$ μg/mL | $AUC_{last}$ μg · h/mL | $V_{SS}$ mL/kg | CL mL/h/kg | MRT h | F % |
|---|---|---|---|---|---|---|---|---|---|---|---|---|
| 1 | H0L0 | 20200524 | i.v. | 1 | 97 | 0.25 | 28.6 | 2390 | 76 | 0.47 | 170 | / |
| 2 | H0L0 | 20200524 | s.c. | 1 | 75 | 40 | 6.61 | 2120 | / | / | 213 | 85 |
| 3 | H1L1 | 20200524 | i.v. | 1 | 143 | 0.25 | 31.7 | 3000 | 71 | 0.33 | 200 | / |
| 4 | H1L1 | 20200524 | s.c. | 1 | 122 | 56 | 9.49 | 3020 | / | / | 221 | 101 |

Figure 9:
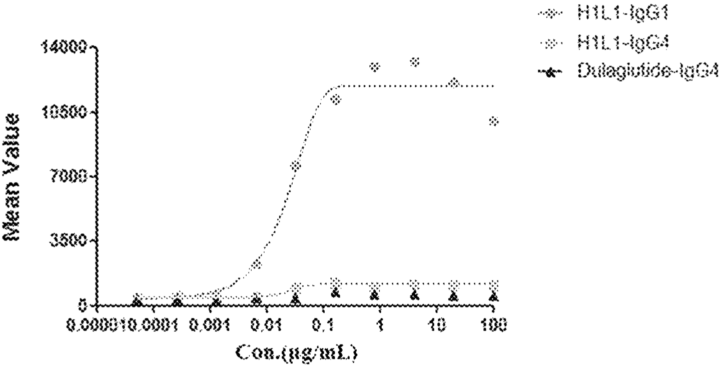
FIG. 9 is a diagram showing the results of ADCC activity of humanized antibodies detected by the luciferase reporter gene system according to an embodiment of the present invention.

FIG. 13 ADCC Activity of Humanized Antibodies Detected by the Luciferase Reporter Gene System Antibody-dependent cell-mediated cytotoxicity (ADCC) means that when IgG antibody specifically binds to antigenic determinants on the surface of target cells through the Fab segment, its Fc segment can bind to effector cells such as FcγR killer cells (NK cells, monocytes-macrophages, neutrophils) to trigger the killing activity of effector cells, and directly kill target cells. In the experiment, the Jurkat-NFAT-Luc-CD16 luciferase reporter cell line stably transfected with CD16 receptor and NFAT (Nuclear Factor of Activated T-cells) reaction original was used. When the Fab segment of the test antibody bound to the antigen on the target cell HEK293T-HumanTrKA cell, the Fc segment of the antibody bound to (Fc γRIIIA) on the surface of the effector cell Jurkat-NFAT-Luciferase-CD16 cell, causing activation of NFAT-related signaling pathways in Jurkat-NFAT-Luciferase-CD16 cells, which in turn led to an increase in expression level of luciferase. The ADCC activity of humanized antibodies was evaluated by detecting the expression level of luciferase of effector cells Jurkat-NFAT-Luciferase-CD16 under the action of different concentrations (100 μg/mL, 20 μg/mL, 4 μg/mL, 0.8 μg/mL, 0.16 μg/mL, 0.032 μg/mL, 0.0064 μg/mL, 0.00128 μg/mL, 0.000256 μg/mL, 0.0000512 μg/mL) of humanized antibodies (H1L1-IgG4, H1L1-IgG1). The results were shown in the FIG. 9 below. In the FIG. 9, Mean Value reflected the expression level of luciferase. The larger the reading, the higher the expression level and the stronger the ADCC activity of the corresponding antibody. The experimental results showed that as the concentration of the antibody increased, the Mean Value of the negative control fusion protein Dulaglutide-IgG4 and the humanized antibody H1L1-IgG4 remained basically unchanged and close to zero, while the Mean Value of the humanized antibody H1L1-IgG1 gradually increased until reaching the plateau value, and half of the peak concentration EC50 was 0.02281 μg/mL; it could be seen that the humanized antibody H1L1-IgG1 had strong ADCC activity, and H1L1-IgG4 basically had no ADCC activity.

Figure 10:
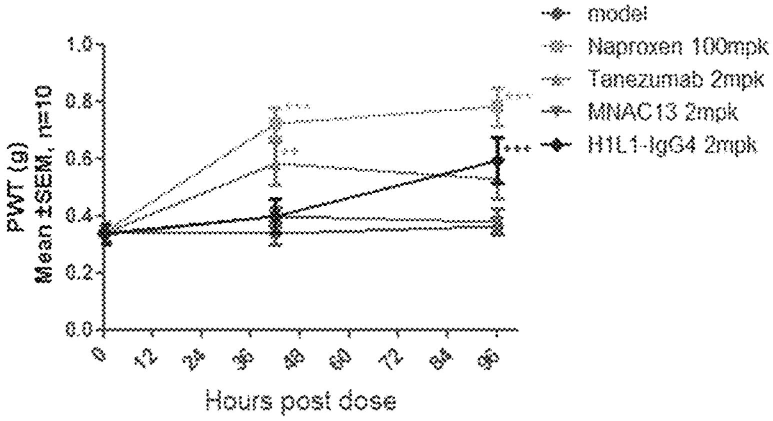
FIG. 10 is a diagram showing the results of in vivo analgesic activity of humanized antibodies evaluated by a complete Freund's adjuvant-induced inflammatory pain model according to an embodiment of the present invention.

Example 14 Evaluation of In Vivo Analgesic Activity of Humanized Antibodies by a Complete Freund's Adjuvant-Induced Inflammation Pain Model Complete Freund's adjuvant-induced inflammatory pain model is a pain model that produces a pain model of chronic inflammatory pain stimulation similar to osteoarthritis and responses by injecting complete Freund's adjuvant in the palms of mice. The pain is measured by the mechanical pain test. The greater the intensity of the mechanical stimulus, the more resistant the animal is to pain. In the experiment, 18-25 g male C57BL/6 mice were selected, and 10 μL of CFA was injected into the center of the sole of the right hind foot of the mouse. After 24 hours of modeling, the mechanical hyperalgesia method was used to test, and the animals with the withdrawal threshold less than 0.5 gram force were screened out. Based on their pain sensitivity, they were randomly divided into solvent control group, naproxen 100 mg/kg dose group, Tanezumab 2 mg/kg dose group, MNAC13 2 mg/kg dose group, H1L1-IgG4 2 mg/kg dose group. There were a total of 5 groups, n=10 per group. Among them, Tanezumab was an anti-NGF monoclonal antibody, and MNAC13 was an anti-TrkA monoclonal antibody. The solvent control group, Tanezumab, MNAC13, and H1L1-IgG4 dose groups were administered by subcutaneous injection, and the mechanical hyperalgesia test was performed after 42 hr and 96 hr respectively. The naproxen dose group was administered intragastrically 2 hours before the test. The results were shown in FIG. 10. The ordinate represented the intensity of mechanical stimulation. The greater the pressure threshold of the mouse paw withdrawal, the better the analgesic effect. The results showed that the positive control group naproxen was tested 2 hours after orally administration at a dose of 100 mg/kg and showed inhibition of mechanical hyperalgesia induced by C57BL/6 mouse CFA model; Tanezumab was tested 42 hours after subcutaneous administration at a dose of 2 mg/kg and showed inhibition of mechanical hyperalgesia induced by C57BL/6 mouse CFA model, while Tanezumab which was tested 96 hours after administration did not show such inhibition; MNAC13 was tested 42 and 96 hours after subcutaneous administration at a dose of 2 mg/kg, and none of them showed inhibition of mechanical hyperalgesia induced by C57BL/6 mouse CFA model. H1L1-IgG4 was tested 96 hours after subcutaneous administration at a dose of 2 mg/kg and showed inhibition of mechanical hyperalgesia induced by the C57BL/6 mouse CFA model, while H1L1-IgG4 which was tested 42 hours after administration did not show such inhibition. Conclusion: H1L1-IgG4 significantly inhibited the mechanical hyperalgesia induced by the C57BL/6 mouse CFA model after 96 hours of subcutaneous administration, and had the activity of relieving inflammatory pain.

Figure 11:
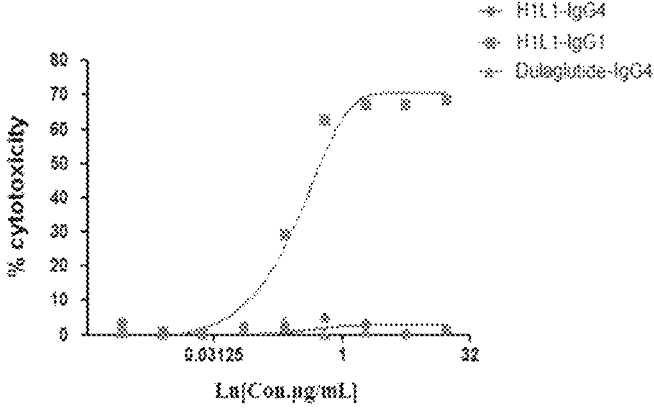
FIG. 11 is a diagram showing the results of the CDC activity of humanized antibodies detected by NIH-3T3-TrkA cell model according to an embodiment of the present invention.

Example 15 CDC Activity of Humanized Antibodies Detected by NIH-3T3-TrkA Cell Model Complement-dependent cytotoxicity (CDC) refers to the cytotoxic effect of complement, that is, through specific antibody binding with the corresponding antigen on the cell membrane surface to form a complex to activate the classical pathway of complement, the formed membrane attack complex exerts a lytic effect on target cells. In the experiment, the cell viability of the target cell NIH-3T3-TrKA was detected by the CCK8 method under the action of different concentrations (16.67 μg/mL, 5.56 μg/mL, 1.85 μg/mL, 0.62 μg/ml, 0.21 μg/ml, 0.069 μg/ml, 0.023 μg/ml, 0.008 μg/ml, 0.003 μg/ml) of humanized antibody (H1L1-IgG4, H1L1-IgG1) and the negative control fusion protein Dulaglutide-IgG4, and the CDC activity of the humanized Anti-TrKA antibody was evaluated. The results were shown in FIG. 11. The results in FIG. 11 showed that with the increase of antibody concentration, the killing effect of humanized antibody H1L1-IgG1 on the target cells NIH-3T3-TrKA cells gradually increased, and the half-peak concentration IC50 was 0.2219 μg/mL; the humanized antibody H1L1-IgG4 and the negative control fusion protein Dulaglutide-IgG4 had basically no killing effect on the target cells NIH-3T3-TrKA cells; it could be seen that the humanized antibody H1L1-IgG1 had strong CDC activity, and H1L1-IgG4 basically had no CDC activity.

Figure 12:
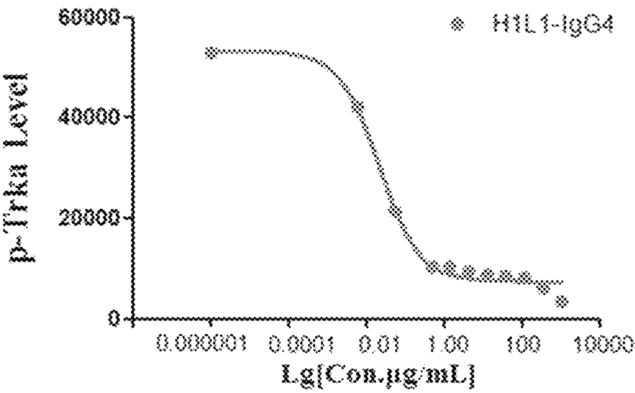
FIG. 12 is a diagram showing the results of the in vitro activity of humanized antibodies evaluated by the NIH-3T3-TrkA cell model according to an embodiment of the present invention.

Example 16 Evaluation of In Vitro Activity of Humanized Antibodies by NIH-3T3-TrkA Cell Model Under NGF stimulation, the level of TrkA protein tyrosine phosphorylation on the NIH-3T3-TrkA cell membrane is up-regulated, and the downstream signaling pathway of TrkA is activated. Humanized Anti-TrKA antibody can bind to the TrkA protein on the surface of NIH-3T3-TrkA cell membrane, inhibit NGF stimulation, and down-regulate the level of TrkA protein tyrosine phosphorylation. In the experiment, the AlphaLISA method was used to detect the down-regulation of the level of TrkA protein tyrosine phosphorylation under the action of different concentrations (1000 μg/mL, 333.33 μg/mL, 111.11 μg/mL, 37.04 μg/mL, 12.35 μg/mL, 4.12 μg/mL, 1.37 μg/mL, 0.45 μg/mL, 0.15 μg/mL, 0.05 μg/mL, 0.017 μg/mL, 0.005 μg/mL) of humanized antibodies, and the in vitro activity of the tested antibody was evaluated. The test results of p-TrkA were shown in FIG. 12. The experimental results showed that the humanized Anti-TrKA antibody H1L1-IgG4 could inhibit the NGF-TrKA signaling pathway and down-regulate the level of TrkA protein tyrosine phosphorylation in a dose-dependent manner. The IC50 value was 0.02072 μg/mL. It could be seen that the humanized Anti-TrKA antibody H1L1-IgG4 could inhibit the activation of the downstream signaling pathway of TrKA by NGF.

The solution of the present invention will be explained below in conjunction with examples. Those skilled in the art will understand that the following examples are only used to illustrate the present invention, and should not be regarded as limiting the scope of the present invention. If the specific technology or condition is not indicated in the examples, the technology or condition described in the literature in the art or the product description is performed. If the reagents or instruments used are not specified by the manufacturer, they are all conventional products that are commercially available.

The invention claimed is:

1. A humanized antibody or antigen-binding fragment thereof capable of specifically recognizing TrkA, wherein the antibody or antigen-binding fragment thereof comprises:

a heavy chain variable region with the VH-CDR1 shown in SEQ ID NO:41, the VH-CDR2 shown in SEQ ID NO:42 or SEQ ID NO:43, and the VH-CDR3 shown in SEQ ID NO: 44;

a light chain variable region with the VL-CDR1 shown in SEQ ID NO:45, the VL-CDR2 shown in SEQ ID NO:46 or SEQ ID NO:47, and the VL-CDR3 shown in SEQ ID NO:48;

a heavy chain framework region sequence; and a light chain framework region sequence;

wherein the heavy chain framework region sequence and the light chain framework region sequence are derived from human IgG antibodies or mutants thereof.

2. The humanized antibody or antigen-binding fragment thereof according to claim 1, wherein the antibody or antigen-binding fragment thereof comprises a heavy chain variable region with the amino acid sequence shown in any one of SEQ ID NO: 2-8, and a light chain variable region with the amino acid sequence shown in any one of SEQ ID NO: 10-13.

3. The humanized antibody or antigen-binding fragment thereof according to claim 1, wherein the antibody or antigen-binding fragment thereof comprises a heavy chain variable region and a light chain variable region selected from:

(a) the heavy chain variable region with the amino acid sequence shown in SEQ ID NO: 2 and the light chain variable region with the amino acid sequence shown in SEQ ID NO: 10;

(b) the heavy chain variable region with the amino acid sequence shown in SEQ ID NO: 4 and the light chain variable region with the amino acid sequence shown in SEQ ID NO: 10; or (c) the heavy chain variable region with the amino acid sequence shown in SEQ ID NO: 4 and the light chain variable region with the amino acid sequence shown in SEQ ID NO: 11.

4. The humanized antibody or antigen-binding fragment thereof according to claim 1, wherein the antibody or antigen-binding fragment thereof specifically recognizes the extracellular region of TrkA.

5. The humanized antibody or antigen-binding fragment thereof according to claim 1, wherein the antibody comprises at least one of a heavy chain constant region and a light chain constant region, and both the heavy chain constant region and the light chain constant region are derived from human IgG antibodies or their mutants.

6. The humanized antibody or antigen-binding fragment thereof according to claim 5, wherein the Fc region of the antibody has S10P, F16A, L17A, R191K mutations and 229 K deletion mutations compared with the human IgG4 wild-type Fc, wherein the human IgG4 wild-type Fc has the amino acid sequence shown in SEQ ID NO: 16.

7. The humanized antibody or antigen-binding fragment thereof according to claim 5, wherein the full-length sequence of the constant region of the antibody is as shown in SEQ ID NO: 14 or 15.

8. The humanized antibody or antigen-binding fragment thereof according to claim 1, wherein the antibody comprises a heavy chain with the amino acid sequence shown in any one of SEQ ID NO: 17 to 23 and a light chain with the amino acid sequence shown in any one of SEQ ID NO: 24 to 27.

9. The humanized antibody or antigen-binding fragment thereof according to claim 1, wherein the antibody is selected from the following heavy chain and light chain:

(a) the heavy chain with the amino acid sequence shown in SEQ ID NO: 17 and the light chain with the amino acid sequence shown in SEQ ID NO: 24;

(b) the heavy chain with the amino acid sequence shown in SEQ ID NO: 19 and the light chain with the amino acid sequence shown in SEQ ID NO: 24; or (c) the heavy chain with the amino acid sequence shown in SEQ ID NO: 19 and the light chain with the amino acid sequence shown in SEQ ID NO: 25.

10. A nucleic acid molecule encoding the humanized antibody or antigen-binding fragment thereof according to claim 1;

wherein the nucleic acid molecule is DNA;

wherein the nucleic acid molecule comprises the nucleotide sequence shown in any one of SEQ ID NO: 30-36 or comprises the nucleotide sequence shown in any one of SEQ ID NO: 37-40.

11. An expression vector carrying the nucleic acid molecule according to claim 10.

12. A recombinant cell expressing the humanized antibody or antigen-binding fragment thereof according to claim 1, or carrying the nucleic acid molecule encoding the humanized antibody or antigen-binding fragment;

wherein the recombinant cell is obtained by introducing the expression vector into a host cell.

13. A pharmaceutical composition comprising the humanized antibody or antigen-binding fragment thereof according to claim 1, or the nucleic acid molecule encoding the humanized antibody or antigen-binding fragment, or the recombinant cell expressing the humanized antibody or antigen-binding fragment, or the recombinant cell carrying the nucleic acid molecule.

14. A method of treating a disease caused by abnormal expression of NGF, abnormal expression of TrkA, or abnormal activity of TrkA in a subject comprising administering to the subject a therapeutically effective amount of the pharmaceutical composition of claim 13, wherein the disease caused by abnormal expression of NGF, abnormal expression of TrkA, or abnormal activity of TrkA is selected from the group consisting of neuropathic pain, inflammatory pain, cancer-related pain, fracture-related pain, surgery-related pain, and, painful bladder syndrome.

15. A method of treating a disease caused by abnormal expression of NGF, abnormal expression of TrkA, or abnormal activity of TrkA in a subject comprising administering to the subject a therapeutically effective amount of the humanized antibody of claim 1, or the nucleic acid molecule encoding the humanized antibody, or the recombinant cell expressing the humanized antibody or antigen-binding fragment, or the recombinant cell carrying the nucleic acid molecule, wherein the disease caused by abnormal expression of NGF, abnormal expression of TrkA, or abnormal activity of TrkA is selected from the group consisting of neuropathic pain, inflammatory pain, cancer-related pain, fracture-related pain, surgery-related pain, and painful bladder syndrome.

16. A kit for detecting TrkA comprising the humanized antibody according to claim 1.

17. A method of detecting TrkA or diagnosing a TrkA-related disease in a subject using a kit comprising the humanized antibody of claim 1, or the nucleic acid molecule encoding the humanized antibody or antigen-binding fragment, or the expression vector carrying the nucleic acid molecule, or the recombinant cell expressing the humanized antibody or antigen-binding fragment, or the recombinant cell carrying the nucleic acid molecule.

* * * * *